US010729823B2

(12) United States Patent
Lee et al.

(10) Patent No.: US 10,729,823 B2
(45) Date of Patent: Aug. 4, 2020

(54) MULTI-UNIT DRUG DELIVERY DEVICES AND METHODS

(71) Applicant: TARIS Biomedical LLC, Lexington, MA (US)

(72) Inventors: Heejin Lee, Bedford, MA (US); Karen Daniel, Newton, MA (US); Matthew Sansone, Dracut, MA (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 14/913,185

(22) PCT Filed: Aug. 19, 2014

(86) PCT No.: PCT/US2014/051672
§ 371 (c)(1),
(2) Date: Feb. 19, 2016

(87) PCT Pub. No.: WO2015/026813
PCT Pub. Date: Feb. 26, 2015

(65) Prior Publication Data
US 2016/0199544 A1    Jul. 14, 2016

Related U.S. Application Data

(60) Provisional application No. 61/877,610, filed on Sep. 13, 2013, provisional application No. 61/867,245, filed on Aug. 19, 2013.

(51) Int. Cl.
*A61M 31/00* (2006.01)
*A61L 31/16* (2006.01)
(Continued)

(52) U.S. Cl.
CPC ............ *A61L 31/16* (2013.01); *A61K 9/0004* (2013.01); *A61K 9/0034* (2013.01);
(Continued)

(58) Field of Classification Search
CPC ..... A61M 31/002; A61M 31/00; A61L 31/16; A61L 31/048; A61L 31/08; A61K 9/0004;
(Continued)

(56) References Cited

U.S. PATENT DOCUMENTS 3,089,815 A    5/1963   Hans et al.
3,854,480 A    12/1974  Zaffaroni
(Continued)

FOREIGN PATENT DOCUMENTS

DE    3332156 A1    3/1985
EP    0572932 A2    12/1993
(Continued)

OTHER PUBLICATIONS

Amark, et al., "Follow-Up of Long-Time Treatment with Intravesical Oxybutynin for Neurogenic Bladder in Children," European Urology, vol. 34 (1998), pp. 148-153.
(Continued)

*Primary Examiner* — Kevin C Sirmons
*Assistant Examiner* — Tezita Z Watts
(74) *Attorney, Agent, or Firm* — Eversheds Sutherland (US) LLP

(57) ABSTRACT

Implantable drug delivery devices include a housing defining a reservoir, a first unit within the reservoir, and a second unit within the reservoir. The first unit contains a drug and the second unit contains a functional agent that facilitates release of the drug. Intravesical drug delivery devices include a housing portion containing a drug formulation and a housing portion containing an excipient, and are configured to release the drug according to a first release profile and the excipient according to a second release profile. Methods include inserting any of these devices into a patient and releasing drug from the device.

31 Claims, 13 Drawing Sheets

(51) Int. Cl.
*A61K 31/7068* (2006.01)
*A61K 47/18* (2017.01)
*A61L 31/08* (2006.01)
*A61L 31/04* (2006.01)
*A61K 9/00* (2006.01)

(52) U.S. Cl.
CPC .......... *A61K 31/7068* (2013.01); *A61K 47/18* (2013.01); *A61L 31/048* (2013.01); *A61L 31/08* (2013.01); *A61M 31/002* (2013.01); *A61K 9/0092* (2013.01)

(58) Field of Classification Search
CPC .. A61K 9/0034; A61K 9/0092; A61K 9/0019; A61K 9/7068; A61K 47/18
See application file for complete search history.

(56) References Cited

U.S. PATENT DOCUMENTS

| | | | |
|---|---|---|---|
| 3,888,975 A | 6/1975 | Ramwell | |
| 3,901,232 A | 8/1975 | Michaels et al. | |
| 3,935,860 A | 2/1976 | Hoff | |
| 3,948,254 A * | 4/1976 | Zaffaroni | A61K 9/0004 128/833 |
| 4,016,251 A | 4/1977 | Higuchi et al. | |
| 4,111,203 A * | 9/1978 | Theeuwes | A61F 9/0017 206/0.5 |
| 4,210,139 A | 7/1980 | Higuchi | |
| 4,235,236 A | 11/1980 | Theeuwes | |
| 4,309,996 A | 1/1982 | Theeuwes | |
| 4,326,522 A | 4/1982 | Guerrero et al. | |
| 4,392,848 A | 7/1983 | Lucas et al. | |
| 4,449,980 A | 5/1984 | Millar et al. | |
| 4,475,916 A | 10/1984 | Himmelstein | |
| 4,578,075 A | 3/1986 | Urquhart et al. | |
| 4,578,263 A | 3/1986 | Whitehead | |
| 4,629,449 A | 12/1986 | Wong | |
| 4,655,219 A | 4/1987 | Petruzzi | |
| 4,678,463 A | 7/1987 | Millar | |
| 4,681,583 A | 7/1987 | Urquhart et al. | |
| 4,731,054 A | 3/1988 | Billeter et al. | |
| 4,871,542 A | 10/1989 | Vilhardt | |
| 4,968,507 A | 11/1990 | Zentner et al. | |
| 4,973,304 A | 11/1990 | Graham et al. | |
| 5,008,112 A * | 4/1991 | DePrince | A61K 9/0004 424/468 |
| 5,057,318 A * | 10/1991 | Magruder | A61K 9/0004 424/423 |
| 5,324,280 A * | 6/1994 | Wong | A61K 9/0004 604/892.1 |
| 5,340,590 A | 8/1994 | Wong et al. | |
| 5,366,738 A | 11/1994 | Rork et al. | |
| 5,441,550 A | 8/1995 | Hassenboehler, Jr. et al. | |
| 5,499,997 A | 3/1996 | Sharpe et al. | |
| 5,516,522 A | 5/1996 | Peyman et al. | |
| 5,551,954 A | 9/1996 | Buscemi et al. | |
| 5,709,874 A | 1/1998 | Hanson et al. | |
| 5,788,980 A | 8/1998 | Nabahi | |
| 5,795,591 A | 8/1998 | Lee et al. | |
| 5,797,898 A | 8/1998 | Santini, Jr. et al. | |
| 5,830,230 A | 11/1998 | Berryman et al. | |
| 5,851,217 A | 12/1998 | Wolff et al. | |
| 5,855,906 A | 1/1999 | McClay | |
| 5,869,081 A | 2/1999 | Jackanicz et al. | |
| 5,972,372 A | 10/1999 | Saleh et al. | |
| 5,989,581 A | 11/1999 | Groenewegen | |
| 6,039,967 A | 3/2000 | Ottoboni et al. | |
| 6,039,968 A | 3/2000 | Nabahi | |
| 6,083,933 A | 7/2000 | Hahn | |
| 6,086,909 A | 7/2000 | Harrison et al. | |
| 6,139,535 A | 10/2000 | Greelis et al. | |
| 6,159,143 A | 12/2000 | Lennox | |
| 6,168,801 B1 | 1/2001 | Heil, Jr. et al. | |
| 6,171,298 B1 | 1/2001 | Matsuura et al. | |
| 6,183,461 B1 | 2/2001 | Matsuura et al. | |
| 6,207,180 B1 | 3/2001 | Ottoboni et al. | |
| 6,283,953 B1 * | 9/2001 | Ayer | A61K 9/0004 424/423 |
| 6,293,923 B1 | 9/2001 | Yachia et al. | |
| 6,398,718 B1 | 6/2002 | Yachia et al. | |
| 6,416,780 B1 | 7/2002 | Passmore et al. | |
| 6,444,224 B1 | 9/2002 | Rathbone et al. | |
| 6,464,999 B1 | 10/2002 | Huo et al. | |
| 6,482,837 B1 | 11/2002 | Wood | |
| 6,491,666 B1 | 12/2002 | Santini, Jr. et al. | |
| 6,524,608 B2 | 2/2003 | Ottoboni et al. | |
| 6,682,473 B1 | 1/2004 | Matsuura et al. | |
| 6,712,784 B2 | 3/2004 | Huang | |
| 6,730,072 B2 | 5/2004 | Shawgo et al. | |
| 6,746,421 B2 | 6/2004 | Yachia et al. | |
| 6,749,617 B1 | 6/2004 | Palasis et al. | |
| 6,753,011 B2 | 6/2004 | Faour | |
| 6,808,522 B2 | 10/2004 | Richards et al. | |
| 6,875,208 B2 | 4/2005 | Santini, Jr. et al. | |
| 6,899,890 B2 | 5/2005 | Kirschner et al. | |
| 6,932,810 B2 | 8/2005 | Ryan | |
| 6,951,654 B2 | 10/2005 | Malcolm et al. | |
| 6,973,718 B2 | 12/2005 | Sheppard, Jr. et al. | |
| 6,976,950 B2 | 12/2005 | Connors et al. | |
| 6,976,951 B2 | 12/2005 | Connors et al. | |
| 6,988,983 B2 | 1/2006 | Connors et al. | |
| 7,005,138 B2 | 2/2006 | Mahashabde et al. | |
| 7,074,178 B2 | 7/2006 | Connors et al. | |
| 7,207,982 B2 | 4/2007 | Dionne et al. | |
| 7,232,421 B1 | 6/2007 | Gambale et al. | |
| 7,521,064 B2 | 4/2009 | Saxena et al. | |
| 7,647,112 B2 | 1/2010 | Tracey et al. | |
| 8,343,516 B2 | 1/2013 | Daniel et al. | |
| 9,017,312 B2 | 4/2015 | Lee et al. | |
| 2003/0059456 A1 | 3/2003 | Malcolm et al. | |
| 2003/0118649 A1 | 6/2003 | Gao et al. | |
| 2003/0118692 A1 | 6/2003 | Wang et al. | |
| 2003/0139800 A1 | 7/2003 | Campbell | |
| 2003/0229263 A1 | 12/2003 | Connors et al. | |
| 2004/0022824 A1 | 2/2004 | Li et al. | |
| 2004/0034332 A1 | 2/2004 | Uhland | |
| 2004/0149294 A1 | 8/2004 | Gianchandani et al. | |
| 2004/0220552 A1 | 11/2004 | Heruth et al. | |
| 2004/0260272 A1 | 12/2004 | Friedman et al. | |
| 2005/0228482 A1 | 10/2005 | Herzog et al. | |
| 2005/0234013 A1 | 10/2005 | Parsons | |
| 2005/0234431 A1 | 10/2005 | Williams et al. | |
| 2005/0238733 A1 | 10/2005 | Henry | |
| 2006/0105010 A1 | 5/2006 | Rahe et al. | |
| 2006/0122689 A1 | 6/2006 | Kocur et al. | |
| 2006/0234978 A1 | 10/2006 | Marcum | |
| 2006/0259118 A1 | 11/2006 | Pal et al. | |
| 2006/0264897 A1 | 11/2006 | Lobl et al. | |
| 2006/0264912 A1 | 11/2006 | McIntyre et al. | |
| 2007/0161967 A1 * | 7/2007 | Fischer, Jr. | A61L 27/54 604/508 |
| 2007/0172507 A1 | 7/2007 | Zupkas et al. | |
| 2007/0172508 A1 | 7/2007 | Zupkas et al. | |
| 2007/0191818 A1 | 8/2007 | Dionne et al. | |
| 2007/0202151 A1 | 8/2007 | Lee et al. | |
| 2007/0254014 A1 | 11/2007 | Ahmed et al. | |
| 2008/0051740 A1 | 2/2008 | Sokal et al. | |
| 2009/0004246 A1 | 1/2009 | Woolfson et al. | |
| 2009/0149833 A1 | 6/2009 | Cima et al. | |
| 2009/0317465 A1 | 12/2009 | Peppas | |
| 2010/0003297 A1 | 1/2010 | Tobias et al. | |
| 2010/0076261 A1 | 3/2010 | Neeman et al. | |
| 2010/0331770 A1 | 12/2010 | Lee et al. | |
| 2011/0060309 A1 * | 3/2011 | Lee | A61K 9/0034 604/500 |
| 2011/0106006 A1 | 5/2011 | Martin et al. | |
| 2011/0152839 A1 | 6/2011 | Cima et al. | |
| 2012/0089122 A1 * | 4/2012 | Lee | A61K 9/0039 604/517 |
| 2012/0203203 A1 | 8/2012 | Lee et al. | |
| 2014/0276636 A1 | 9/2014 | Lee et al. | |

(56) References Cited

U.S. PATENT DOCUMENTS

| | | | |
|---|---|---|---|
| 2015/0165177 | A1 | 6/2015 | Giesing |
| 2015/0209277 | A1 | 7/2015 | Lee et al. |
| 2015/0250717 | A1 | 9/2015 | Giesing et al. |

FOREIGN PATENT DOCUMENTS

| | | | |
|---|---|---|---|
| WO | 1997/027840 A1 | 8/1997 | |
| WO | 1997/044021 A1 | 11/1997 | |
| WO | 1998/031415 A1 | 7/1998 | |
| WO | 1999/018884 A1 | 4/1999 | |
| WO | 2000/040234 A1 | 7/2000 | |
| WO | 2001/067991 A1 | 9/2001 | |
| WO | 2002/000203 A1 | 1/2002 | |
| WO | 2002/005800 A2 | 1/2002 | |
| WO | 2002/085428 A2 | 10/2002 | |
| WO | 2003/009882 A2 | 2/2003 | |
| WO | 2004089457 A1 | 10/2004 | |
| WO | 2005/115245 A1 | 12/2005 | |
| WO | 2007/115259 A2 | 10/2007 | |
| WO | 2008/051889 A1 | 5/2008 | |
| WO | 2008/115536 A2 | 9/2008 | |
| WO | 2009/029958 A2 | 3/2009 | |
| WO | 2013064745 A1 | 5/2013 | |
| WO | 2014138214 A1 | 9/2014 | |
| WO | 2014144066 A1 | 9/2014 | |

OTHER PUBLICATIONS

Au, et al., "Methods to Improve Efficacy of Intravesical Mitomycin C: Results of a Randomized Phase III Trial," Journal of the National Cancer Institute, vol. 93, No. 8 (Apr. 18, 2001).
Bade, et al., "A Placebo-Controlled Study of Intravesical Pentosanpolysulphate for the Treatment of Interstitial Cystitis," British Journal of Urology, vol. 79 (1997), pp. 168-171.
Beiko, et al., "Urinary Tract Biomaterials," The Journal of Urology, vol. 171 (Jun. 2004), pp. 2438-2444.
Birch, et al., "Absorption Characteristics of Lignocaine Following Intravesical Instillation," Scand J Urol Nephrol, vol. 28 (1994), pp. 359-364.
Burmeister, et al., Intravesical instillation of trospium chloride, oxybutynin and verapamil for relaxation of the bladder detrusor muscle. A placebo controlled, randomized clinical test, Arzneimittelforschung, vol. 48, No. 5 (May 1998); pp. 486-491. Abstract.
Carr, et al., "Evaluation of a transoral delivery system for topical anesthesia," J Am Dent Assoc, vol. 132 (2001), pp. 1714-1719.
Clemens, et al., "Interstitial Cystitis and Painful Bladder Syndrome," Urological Diseases in America, (2007), pp. 125-154.
Collins, et al., "How Common is Prostatitis? A National Survey of Physician Visits," The Journal of Urology, vol. 159 (Apr. 1998), pp. 1224-1228.
Curhan, et al., "Epidemiology of Interstitial Cystitis: A Population Based Study," The Journal of Urology, vol. 161 (Feb. 1999), pp. 549-552.
Dentipatch (lidocaine) Patch [Noven Pharmaceuticals, Inc.], downloaded from http://dailymed.nlm.nih.gov/dailymed/fdaDrugXsl.cfm?id=1543&type=display on Feb. 22, 2007.
Erickson, et al., "Interstitial Cystitis," Int Urogynecol J, vol. 9 (1998), pp. 174-183, Springer-Verlag London Ltd.
Estebe, et al., "Alkalinization of Intracuff Lidocaine: Efficacy and Safety," Anesth Analg, vol. 101 (2005), pp. 1536-1541, International Anesthesia Research Society.
Fraser, et al., "The Future of Bladder Control—Intravesical Drug Delivery, a Pinch of Pepper, and Gene Therapy," Reviews in Urology, vol. 4, No. 1 (2002).
Gammaitoni, et al., "Safety and Tolerability of the Lidocaine Patch 5%, a Targeted Peripheral Analgesic: A Review of the Literature," J Clin Pharmacol, vol. 43 (2003), pp. 111-117, American College of Clinical Pharmacology.
Gasión, et al., "Improving Efficacy of Intravesical Chemotherapy," European Urology, vol. 50 (2006), pp. 225-234, Elsevier B.V.
Giannantoni, et al., "New Frontiers in Intravesical Therapies and Drug Delivery," European Urology, vol. 50 (2006), pp. 1183-1193, Elsevier B.V.
Grayson, et al., Molecular release from a polymeric micro reservoir device: Influence of chemistry, polymer swelling, and loading on device performance, J_ Biomed Mat Res, vol. 69A, No. 3 (2004), pp. 502-512.
Henry, et al., "Alkalinized Intravesical Lidocaine to Treat Interstitial Cystitis: Absorption Kinetics in Normal and Interstitial Cystitis Bladders," Urology, vol. 57, Supplement 6A (Jun. 2001), p. 119.
Highley, et al., "Intravesical Drug Delivery Pharmacokinetic and Clinical Considerations," Clinical Pharmacokinetic, vol. 37, No. 1 (Jul. 1999), pp. 59-73, Adis International Limited.
Jiranantarat, et al., "Analgesic Effect of Intraperitoneal Instillation of Bupivacaine for Postoperative Laparoscopic Cholecystectomy," J Med Assoc Thai, vol. 85, Suppl. 3 (Sep. 2002), pp. S897-S903.
Kim, et al., "Antimuscarinic Agents Exhibit Local Inhibitory Effects on Muscarinic Receptors in Bladder-Afferent Pathways," Urology, vol. 65, No. 2 (2005), pp. 238-242, Elsevier Inc.
Larsson, et al., "Effect of Intraperitoneal Instillation of 32% Dextran 70 on Postoperative Adhesion Formation After Tubal Surgery," Acta Obstet Gynecol Scand, vol. 64 (1985), pp. 437-441.
Li, et al. "Water Based Silicone Elastomer Controlled Release Tablet Film Coating III—Drug Release Mechanisms," Drug Development and Industrial Pharmacy, vol. 15, No. 12 (1989), pp. 1943-1968, Marcel Dekker, Inc.
Malmstrom, Per-Uno, "Intravesical therapy of superficial bladder cancer," Critical Reviews in Oncology Hematology, vol. 47 (2003), pp. 109-126, Elsevier Science.
Morimoto, et al., "Management of Patients with Recurrent Nephrosis and Intractable Edema by Intraperitoneal Instillation of Icodextrin Solution," Peritoneal Dialysis International, vol. 28, No. 5 (Sep. 2008), pp. 559-561.
Parsons, C. Lowell, "Successful Downregulation of Bladder Sensory Nerves with Combination of Heparin and Alkalinized Lidocaine in Patients with Interstitial Cystitis," Urology, vol. 65, No. 1 (2005), pp. 45-48.
Russell, et al., "High-performance liquid chromatographic determination of 17β-estradiol and 17β-estradiol-3-acetate solubilities and diffusion coefficients in silicone elastomeric intravaginal rings," Journal of Chromatography B, vol. 744 (2000), pp. 157-163, Elsevier Science B.V.
Saitoh, et al., "Effects of Intravesical Instillation of Resiniferatoxin on Bladder Function and Nociceptive Behavior in Freely Moving, Conscious Rats," The Journal of Urology, vol. 179 (Jan. 2008), pp. 359-364, American Urological Association, U.S.A.
Santus, et al., "Osmotic drug delivery: a review of the patent literature," Journal of Controlled Release, vol. 35 (1995), pp. 1-21.
Spratt, et al., "Clinical Delivery System for Intraperitoneal Hyperthermic Chemotherapy," Cancer Research, vol. 40 (Feb. 1980), pp. 256-260.
Theeuwes, Felix, "Elementary Osmotic Pump," Journal of Pharm Sci, vol. 64, No. 12 (Dec. 1975), pp. 1987-1991.
Theoharides, et al., "Painful Bladder Syndrome/Interstitial Cystitis: Current Concepts and Role of Nutraceuticals," Seminars in Preventive and Alternative Medicine, vol. 2 (2006), pp. 6-14, Elsevier Inc.
Thombre, et al., "Mechanism of Water Transport in Controlled Porosity Osmotic Devices," Journal of Membrane Science, vol. 40 (1989), pp. 279-310, Elsevier Science Publishers B.V.
Tyagi, et al., "Local Drug Delivery to Bladder Using Technology Innovations," Urological Clinics of North America, vol. 33 (2006), pp. 519-530, Elsevier Inc.
Vassileva, et al., "Novel biocompatible intraperitoneal drug delivery system increases tolerability and therapeutic efficacy of paclitaxel in a human ovarian cancer xenograft model," Cancer Chemother Pharmacol, vol. 60 (2007), pp. 907-914, Springer-Verlag.
Verma, et al., "Formulation aspects in the development of osmotically controlled oral drug delivery systems," Journal of Controlled Release, vol. 79 (2002), pp. 7-27, Elsevier Science B.V.
Walker, et al., "Intravesical Chemotherapy: In Vitro Studies on the Relationship Between Dose and Cytotoxicity," Urological Research, vol. 14 (1986), pp. 137-140, Springer-Verlag.
Walter, et al., "Bioavailability of Trospium Chloride After Intravesical Instillation in Patients with Neurogenic Lower Urinary Tract

(56) References Cited

OTHER PUBLICATIONS

Dysfunction: A Pilot Study," Neurourology and Urodynamics, vol. 18 (1999), pp. 447-453, Wiley-Liss, Inc.

Woolfson, et al., "Design of a silicone reservoir intravaginal ring for the delivery of oxybutynin," Journal of Controlled Release, vol. 91 (2003), pp. 465-476, Elsevier B.V.

Woolfson, et al., "Design of an intravaginal ring for the controlled delivery of 17β-estradiol as its 3-acetate ester," Journal of Controlled Release, vol. 61 (1999), pp. 319-328, Elsevier Science B.V.

Wright, et al., Pumps/Osmotic, Encyclopedia of Controlled Drug Delivery, vol. 2 (1999), pp. 896-920, New York; John Wiley.

Wright, et al., "DUROS® Osmotic Pharmaceutical Systems for Parenteral & Site-Directed Therapy,", Drug Delivery Technologies: Implantable Technology, vol. 3, No. 1, 2003, pp. 1-15 (http://www.drugdeliverytech.com/cgi-bin/articles.cgi?idArticle=115).

Singh et al., Osmotic Pump Drug Delivery System: A Noval Approach, J. Drug Delivery & Therapeutics, 3(5) 156-62 (2013).

International Search Report and Written Opinion for International Application No. PCT/US2014/051672, dated Jan. 16, 2015 (11 pages).

Australian Office Action for AU Application No. 2014309012 dated Jul. 20, 2018 (3 pages).

Chinese Office Action for CN Application No. 201480044009.0 dated Jun. 28, 2018 (13 pages).

Japanese Office Action for JP Application No. 2016-536377 dated Jun. 28, 2018 (6 pages with English translation).

Russian Office Action for RU Application No. 20116108968/14 dated Jun. 26, 2018 (14 pages with English translation).

\* cited by examiner

A

B

C

D

E

F

G

H

I

MULTI-UNIT DRUG DELIVERY DEVICES AND METHODS

TECHNICAL FIELD

This disclosure generally relates to controlled drug delivery to patients, and more particularly relates to medical devices for controlled drug release, including but not limited to devices deployable in the urinary bladder for release of drug into the bladder.

BACKGROUND

Various implantable drug delivery devices are known in the art. For example, U.S. Patent Application Publication No. 2007/0202151 to Lee et al. and U.S. Patent Application Publication No. 2009/0149833 to Cima et al. describe drug delivery devices for minimally invasive deployment and retention in a cavity or lumen in a patient, such as the bladder. The devices resist excretion, such as in response to the forces associated with urination. For example, the devices may include a retention frame, which may be configured into a relatively low profile for deployment into the body, and once implanted may assume a relatively expanded profile to facilitate retention. The devices may provide controlled release of drug over an extended period in a predefined manner. In some embodiments, the devices include a water-permeable tube that defines a drug reservoir for housing a drug and at least one aperture for releasing the drug. Osmotic pumping or diffusion may be the dominant mechanism by which the drug is released from the reservoir. Highly water-soluble drugs, such as lidocaine hydrochloride, may be released via osmotic pressure at therapeutically useful rates over an extended period. In other embodiments, the device may be configured to release lower solubility or other drugs primarily or exclusively via diffusion.

It would be desirable, however, to provide improved drug delivery devices and systems. For example, it would be desirable to provide devices, systems, and methods in which relatively lower solubility drugs can be released at therapeutically useful rates by an osmotic pressure means over an extended period. It would also be desirable to provide implantable drug delivery devices and systems capable of delivering a variety of active agents at a selected release kinetics profile and to provide additional techniques, structures, and/or formulations to enhance control of drug release in vivo, for example from a device deployed in the bladder.

SUMMARY

In one aspect, an implantable drug delivery device is provided, including a housing defining a reservoir, a first unit contained within the reservoir and a second unit contained within the reservoir in a position distinct from the first unit. The first unit contains a drug and the second unit contains a functional agent which facilitates in vivo release of the drug from housing.

In another aspect, an intravesical drug delivery device is provided, including a first housing portion loaded with a drug formulation which includes a drug, and a second housing portion loaded with an excipient. The device is configured to release the drug according to a first release profile and is configured to release the excipient according to a second release profile which differs from the first release profile.

In yet another aspect, a method of administering a drug to a patient is provided, including inserting a drug delivery device as disclosed herein into a patient, and releasing the drug from the inserted device.

DETAILED DESCRIPTION

Figure 1:
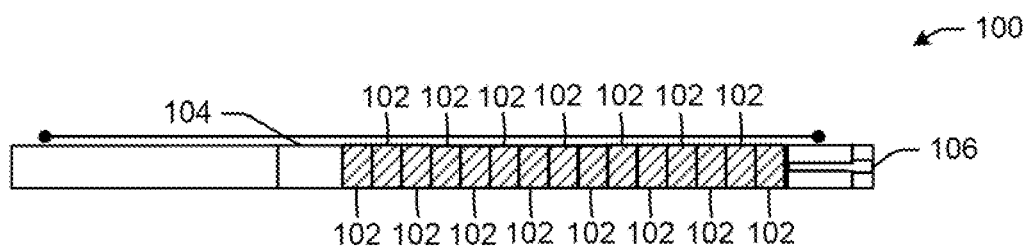
FIG. 1 is a cross-sectional view of an embodiment of a prior art drug delivery device.

Devices are provided that can be inserted in a body cavity or lumen of a patient for the purpose of delivering drug locally or regionally about an implantation site. In one embodiment, the devices contain units of drug and separate units of a second agent that promotes drug release. In vitro examples show improvements to both the short and long-term drug release profiles compared to comparable single unit devices. Moreover, these devices advantageously enable delivery of low solubility drugs to patients via osmotic release devices. This is especially useful for drugs that are difficult to reformulate into more highly soluble forms. Also, osmotic release is generally preferable to diffusion-based release when drug solubility depends significantly on the pH of the release media and it is desirable to reduce the pH dependency of the drug release.

For the purposes of the present disclosure, the term "implantation site" generally refers to a site within the body of a human patient or other animal. The implantation site can be any genitourinary site, such as the bladder, urethra, ureters, kidneys, prostate, seminal vesicles, ejaculatory duct, vas deferens, vagina, uterus, fallopian tubes, ovaries or any other location within a urological or reproductive system of the body, among other locations. In particular embodiments, the implantation site is the bladder.

In certain embodiments, the devices are designed to be deployed through natural orifices and lumens of the body in minimally invasive deployment procedures. For example, the devices may have a deployment shape suited for deployment through a natural lumen of the body. The devices also are designed to be retained in the body once implanted, such as by achieving a retention shape upon implantation or by anchoring within the body. In particular embodiments, the devices can be deployed through the urethra into the bladder and can overcome the forces of urination once implanted for retention in the bladder.

Once implanted, the devices can release one or more drugs over an extended period. The drug may be released by osmotic pumping through an opening in the device, by diffusing through a surface of the device, by diffusing from an opening in the device, or a combination thereof. The drug release may be continuous and in accordance with a pre-defined release profile.

In certain embodiments, the devices are loaded with one or more drug units and one or more functional agent units. As used herein, the term "functional agent" refers to agents or excipients that facilitate in vivo controlled release of a drug from the device. For example, functional agents may include osmotic agents, drug solubilizing agents, drug stabilizing agents, permeation enhancing agents, or combinations thereof. The functional agent may be selected based on the drug(s) to be delivered from the device. For example, the drug to be delivered may be a low solubility drug and the functional agent may include an osmotic agent to facilitate in vivo osmotic release of the drug.

As used herein, the term "low solubility" refers to a drug having a solubility from about 0.001 mg/mL to about 10 mg/mL water at 37° C. As used herein, the term "high solubility" refers to a drug having a solubility above about 10 mg/mL water at 37° C. The solubility of the drug may be affected at least in part by its form. For example, a drug in the form of a water soluble salt may have a high solubility, while the same drug in base form may have a low solubility.

With conventional drug delivery devices, high solubility drugs generally may be suited for release according to an induced osmotic pressure gradient, while low solubility drugs may be suited for release via diffusion through the wall or passageway in the drug housing. The devices disclosed herein are able to deliver a variety of drugs via various release modes and release kinetics profiles, and to provide additional techniques, structures, and/or formulations to enhance control of drug release in vivo.

Whether the selected drug has a high or low solubility, it is to be delivered (i.e., released from the delivery device) at a therapeutically effective rate, which may require the addition of one or more functional agents (e.g., an osmotic agent to increase water flux, solubilizing or solubility enhancing agent, pH adjusting agent, or stability enhancing agent). Generally, the combination of the solubility of the selected drug in the presence or absence of functional agents, if any, and osmotic water flux will determine the release rate and duration, and such combination can be configured for the rate and duration to be within a therapeutically effective range.

The devices and methods disclosed herein build upon those described in U.S. Patent Application Publication No. 2010/0331770 to Lee et al., U.S. Patent Application Publication No. 2011/0152839 to Cima et al., and U.S. Patent Application Publication No. 2012/0203203 to Lee et al., which are incorporated by reference herein.

I. Implantable Drug Delivery Devices

Embodiments of implantable drug delivery devices disclosed herein generally include a housing defining a reservoir, and first and second units contained within the reservoir. For example, the housing may be an elongated, annular tube and the reservoir may be the lumen of the annular tube.

The first unit(s) include a drug or active pharmaceutical ingredient to be delivered to a patient, and the second unit(s) include a functional agent that facilitates in vivo release of the drug from the housing. The first and second units are located at distinct positions within the reservoir. That is, the first and second units are distinct and separate from one another. For example, the first and second units may be solid tablets that are adjacently positioned in the reservoir.

As shown in FIG. 1, a conventional drug delivery device 100 includes multiple identical tablets 102 positioned in a reservoir 104. (For purposes of clarity and ease of comparison with other illustrated embodiments, the device 100 is shown in a linear shape, which may be useful during the process of inserting the device into the patient.) The tablets 102 include the drug to be delivered and, optionally, one or more excipients. Once implanted, the device 100 releases the drug by osmotic pumping through an opening 106 in the device 100. However, the release mode and kinetics of the drug are limited by the tablet formulation, as well as by the characteristics of the materials of construction of the housing.

Figure 2:
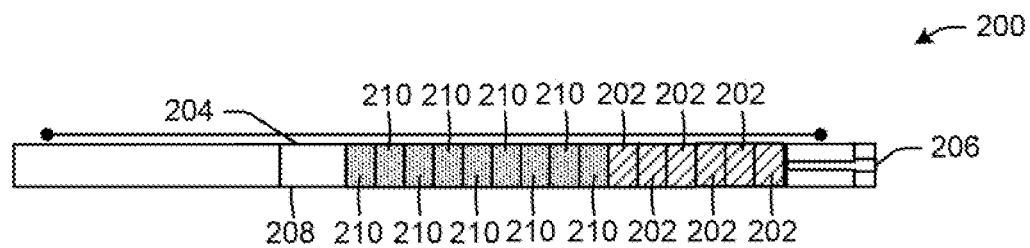
FIG. 2 is a cross-sectional view of one embodiment of a multi-unit drug delivery device.

One embodiment of the present disclosure is shown in FIG. 2. Implantable drug delivery device 200 includes a housing 208, which defines a reservoir 204. In contrast to device 100, device 200 includes a plurality of first units 202, which include a drug, and a plurality of second units 210, which include a functional agent, that are contained within the reservoir 204. The first and second units 202, 210 are located in distinct positions within the reservoir 204. This arrangement may be particularly advantageous, as detailed below.

The device structure, in combination with the drug and functional agent formulations, may be designed to release the drug and functional agent via osmosis and/or diffusion.

FIG. 2 illustrates a device 200 that is configured to operate as an osmotic pump. The device housing 208 includes a wall that is readily permeable to water but not to the drug to be delivered, and a drug that cannot readily diffuse through the wall of the housing 208. That is, the water permeable portion may be substantially impermeable to the drug in aqueous solution. The water permeable wall portion may define at least part of the reservoir 204. After the device is deployed into a patient, water (or urine if in the bladder) permeates through the wall, enters the reservoir 204, and solubilizes the first and/or second units 202, 210. Alternatively, or in combination with a water permeable wall portion, the housing may include at least one aperture configured to permit a fluid to enter the reservoir in vivo. For example, the housing and/or any water permeable wall portions may be silicone, a thermoplastic polyurethane, ethylene-co-vinyl acetate (EVA), or a combination thereof.

Injection of some portion of a solubilization fluid into the reservoir prior to implantation may expedite the hydration process of tablets or formulations therein if needed. In an embodiment, the device is configured to receive at least a portion of the aqueous fluid needed to solubilize the functional agent and drug prior to implantation. For example, the fluid may be delivered into the device reservoir via a needle and syringe. In one embodiment, a portion of the housing includes a low durometer material suitable for penetration by a needle or other instrument. For example, the housing may include a coaxial spacer including a low durometer material portion surrounded by a high durometer material portion. In another example, the housing may include a uni-directional hermetic seal feature.

Following implantation, an osmotic pressure gradient develops between the interior and exterior of the device housing 208, and once sufficient pressure is achieved, solubilized drug is released from the reservoir 204 through at least one drug release orifice 206, which is in fluid communication with the reservoir 204, at a controlled rate, driven by osmotic pressure in the reservoir 204. Such a release mode may be referred to herein as "osmotic release" or "osmotic pumping."

Figure 3:
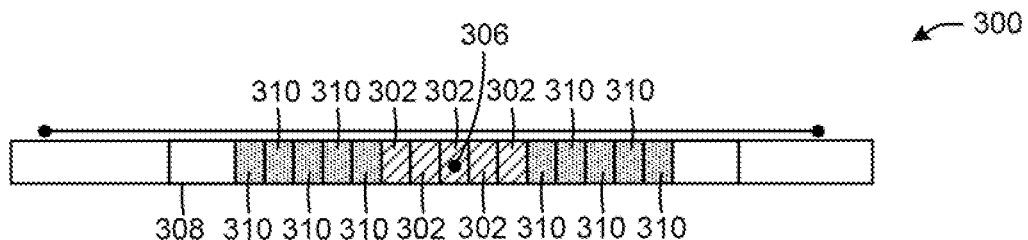
FIG. 3 is a cross-sectional view of another embodiment of a multi-unit drug delivery device.

As shown in FIG. 2, the drug release orifice 206 may be provided in an end plug located at an end of tubular housing 208. Such end plugs, also referred to as "spacer orifices," are described in more detail in PCT Application No. PCT/US14/20703, filed Mar. 5, 2014, which is incorporated herein by reference. FIG. 3 illustrates another embodiment of an osmotic device 300, which includes a drug release orifice 306 in the sidewall of the housing 308, the aperture being configured to allow solubilized drug to pass therethrough.

Figure 17:
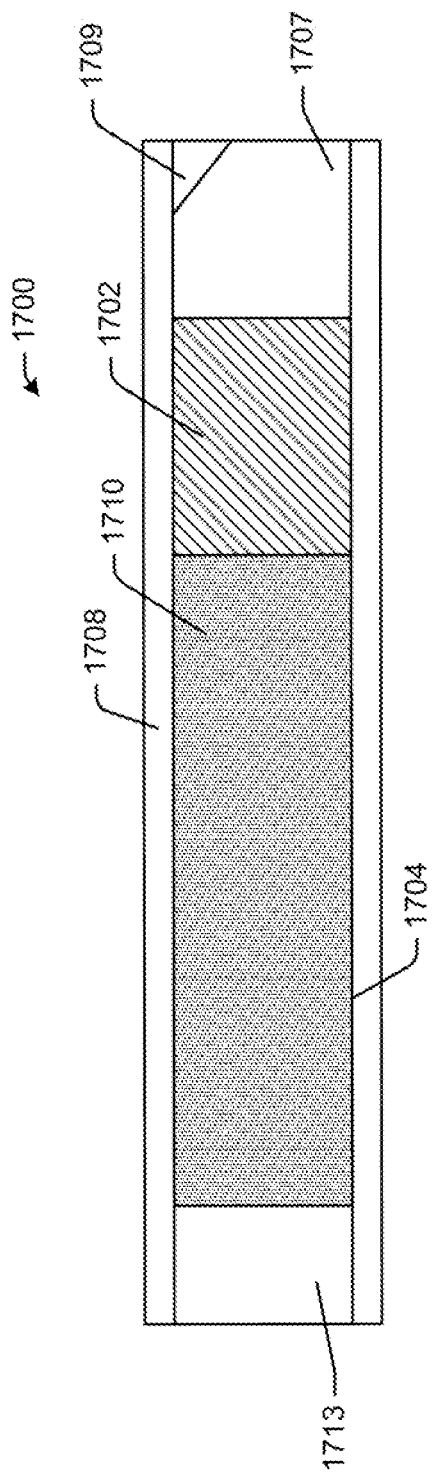
FIG. 17 is a cross-sectional view of one embodiment of a multi-unit drug delivery device.

As shown in FIG. 17, the drug delivery device 1700 may include a restraining plug 1707 at an end of tubular housing 1708. In this embodiment, the restraining plug 1707 controls release of the drug by the transient formation of one or more microchannels between the elastic portion of the housing 1708 and the restraining plug. For example, osmotic tablets 1710 and drug tablets 1702 may be contained in reservoir 1704, which is bounded by a sealed end 1713 and the restraining plug 1707, which may be held in place by adhesive 1709, which secures one part of the restraining plug to the housing without impeding the transient formation of microchannels between another part of the restraining plug and housing (e.g., in an area away from the adhesive). Such restraining plug/microchannels are described in more detail in PCT Application No. PCT/US14/28317, filed Mar. 14, 2014, which is incorporated herein by reference.

In certain embodiments, the first unit, i.e., the drug unit, is located closer than the second unit, i.e., the functional agent unit, to the drug release orifice, drug permeable wall portion, or restraining plug. This arrangement has been shown to be particularly advantageous in terms of achieving therapeutically effective rates of release of drug for certain drugs, such as low solubility drugs.

When osmotic release is the desired drug release mode, the functional agent in the second units may include an osmotic agent that facilitates osmotic release of the drug. For example, the osmotic agent may have a higher solubility than the drug, such that the osmotic agent expedites solubilization and/or subsequent release of the drug. This beneficially allows for the delivery of low solubility or other drugs typically only delivered via diffusion, from osmotic delivery-based devices.

The device 200 may exhibit an induction period while a sufficient volume of functional agent and/or drug are solubilized to achieve the osmotic pressure gradient. Subsequently, the device 200 may exhibit a zero-order release rate for an extended period, followed by a reduced, non-zero-order release rate over a decay period. A desired delivery rate can be achieved by controlling/selecting various parameters of the device, including but not limited to the surface area and thickness of the water permeable wall; the permeability to water of the material used to form the wall; the shape, size, number and placement of the apertures 206; and the dissolution profiles of the drug and functional agent.

The devices described herein may also be configured to release drug via diffusion, alone or in combination with osmotic release. The device may be configured to allow the solubilized drug to pass through a portion of the housing or one or more apertures therein.

In certain embodiments, a water permeable wall portion of the housing is also permeable to the drug in aqueous solution, such that solubilized drug is released via the wall portion, also referred to herein as "trans-wall diffusion." After the device is implanted, water or urine permeates through the wall, enters the reservoir, and solubilizes the functional agent and/or drug. The drug then diffuses directly through the wall at a controlled rate, due to a drug concentration gradient between the interior and the exterior of the device. For example, the housing and/or any water or drug permeable wall portions may be silicone, a thermoplastic polyurethane, ethylene-co-vinyl acetate (EVA), or a combination thereof.

In certain embodiments, the housing has no release orifice and is configured to release the drug through at least one drug permeable wall bounding the reservoir. For example, the drug permeable wall may include a disk stabilized in the lumen of a tube at or near an end of the tube, optionally sandwiched between an inner washer and an outer washer. Drug permeable walls are described in more detail in U.S. patent application Ser. No. 14/216,112, filed Mar. 17, 2014, which is incorporated by reference herein. In other embodiments, the drug permeable wall is part of a sidewall of a tubular housing, or part of an end plug located at the end of a tubular housing.

Alternatively, or in combination with a water permeable wall portion, the housing may include at least one aperture configured to permit a fluid to enter the reservoir in vivo. The housing may also include one or more apertures or passing pores configured to permit solubilized drug to pass therethrough.

As described above, the device may also be configured to receive at least a portion of the water or fluid needed to solubilize the functional agent and drug prior to implantation, for example via a needle and syringe.

The device may exhibit a zero-order release rate for an extended period, followed by a reduced, non-zero-order release rate over a decay period. Zero-order release may begin relatively quickly, as the drug may be immediately available to diffuse across the housing wall once solubilized. The delivery rate is affected by the surface area and thickness of the wall; the permeability to water and drug of the material used to form the wall; the charge or particle size of the drug; and the dissolution profile of the drug and functional agent, among other factors. In embodiments in which the drug is released via one or more apertures or passing pores, a number or combination of apertures or passing pores can be used, which may also affect the overall release rate attributable to diffusion.

Figure 4:
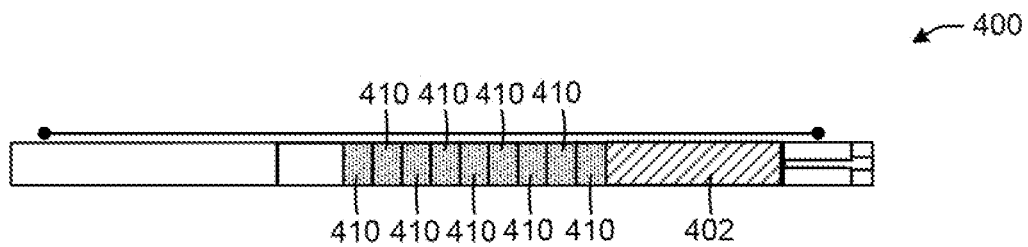
FIG. 4 is a cross-sectional view of another embodiment of a multi-unit drug delivery device.
Figure 5:
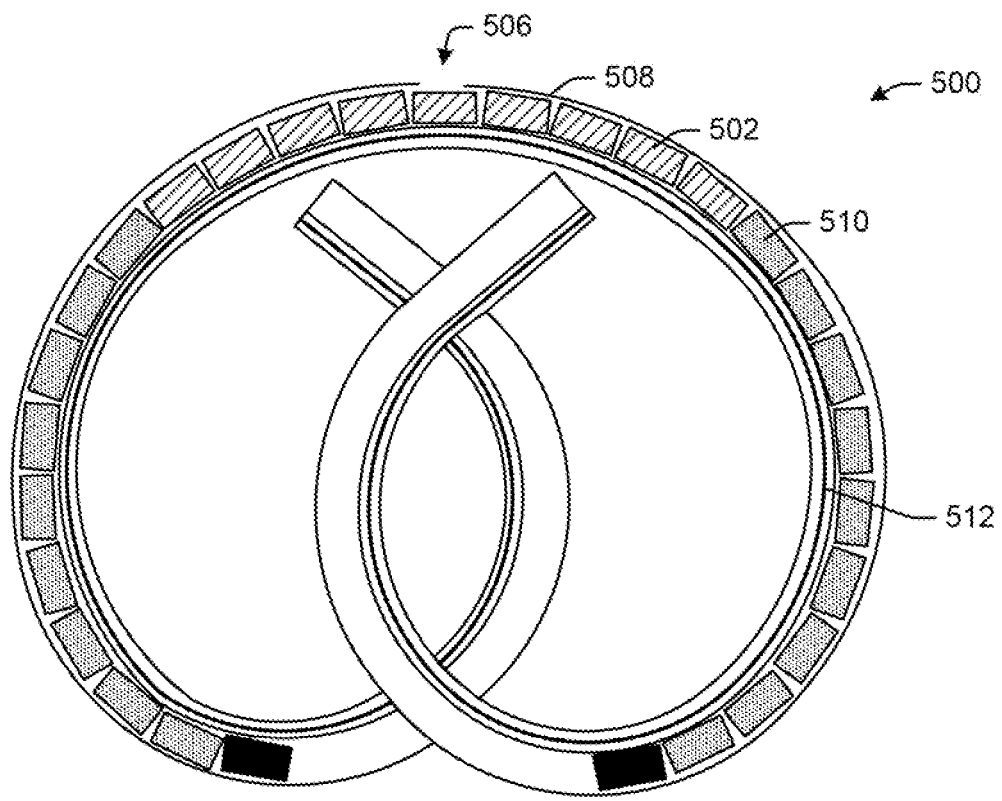
FIG. 5 is a cross-sectional view of one embodiment of a multi-unit drug delivery device.

In certain embodiments, the first unit and/or the second unit is in the form of a solid tablet. For example, as shown in FIG. 4, first unit 402 is in powdered form, while second units 410 are in the form of solid tablets. In other embodiments, as shown in FIGS. 2 and 3, both the first and second units are in the form of solid tablets. In certain embodiments, the solid tablets are configured as "mini-tablets" as described in U.S. Pat. No. 8,343,516 to Daniel et al. In embodiments, as shown in FIG. 5, the device 500 contains a plurality of first units 502 in solid tablet form and a plurality of second units 510 in solid tablet form.

In certain embodiments, each drug unit tablet includes a relatively high weight fraction of the drug and a relatively low weight fraction of excipients. For example, each drug tablet may include more than 50% drug by weight, which permits loading a relatively small device with a therapeutically effective amount of drug. The release rate of drug from the device may be predominately controlled by the combined properties of the functional agent and drug housing and may be altered by adjusting the housing characteristics, such as its thickness and permeability, as well as the functional agent formulation.

The implantable device may be designed for deployment into and retention within a portion of the body, such as the bladder. The device may be flexible so that the device can be deformed for insertion, yet once implanted the device may resist excretion in response to the forces of urination or other forces. In one embodiment, the drug loaded device is flexible or deformable despite being loaded with solid drug unit and/or functional agent unit tablets, as each drug unit may be permitted to move with reference to adjacent drug units. In particular, interstices or breaks between the individual drug units may form reliefs that permit deformation of the device, while allowing the individual units to retain their solid form, as described in U.S. Patent Application Publication No. 2010/0331770 to Lee et al.

Figure 6:
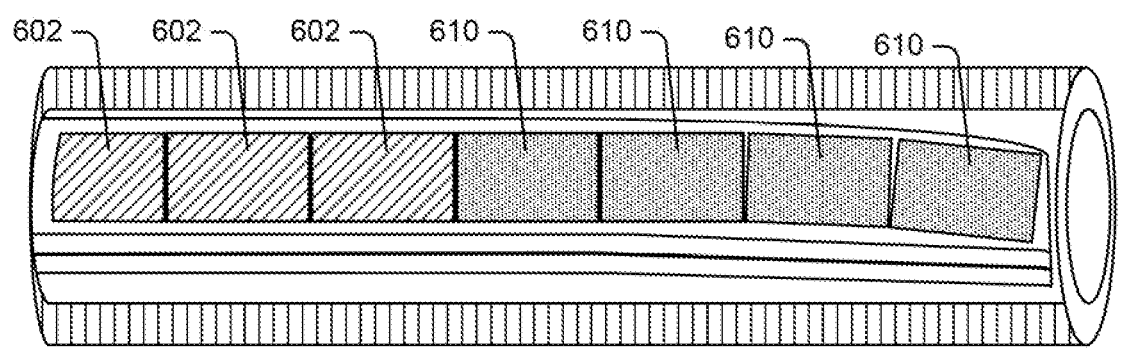
FIG. 6 is a perspective view of a portion of the multi-unit drug delivery device of FIG. 5.

Some solid drug and/or functional agent payloads are flexible overall, including powdered units 402, as shown in FIG. 4, or payloads formed from individual solid tablets 602, 610 that can move with reference to each other, as shown in FIG. 6.

As described above, the device housing may be formed at least partially of a water-permeable material. For example, the housing may be formed from a water-permeable material that permits water to diffuse into the drug housing along its entire length, a portion thereof, or at one or both ends of the device.

Figure 15A:
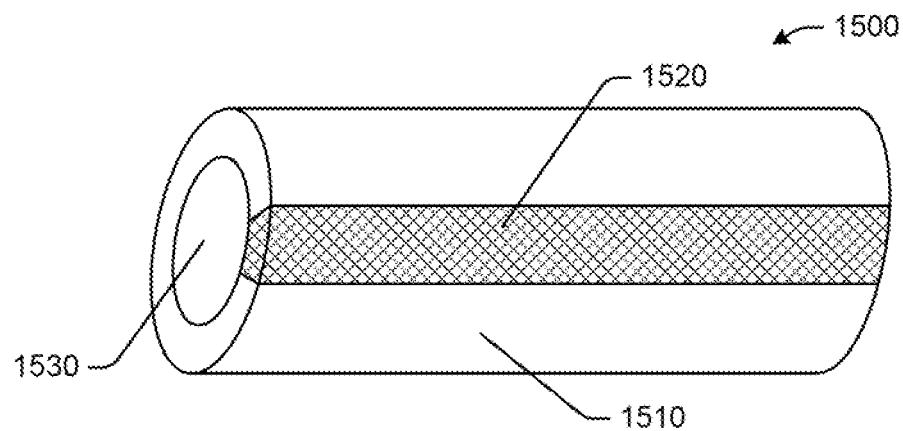
FIGS. 15A-15B are perspective and cross-sectional views, respectively, of one embodiment of the housing for a drug delivery device.
Figure 15B:
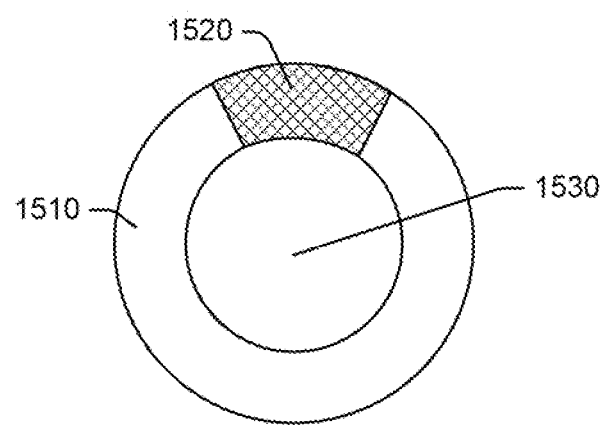

In a particular embodiment, the housing is in the form of one or more elongated annular tubes, wherein the annular tube includes two wall portions, one being water permeable and the other being water impermeable. One embodiment of the annular tube is shown in FIGS. 15A-B. Here, the annular tube 1500 includes water impermeable wall portion 1510 and water permeable wall portion 1520. Upon insertion into the patient, water permeates into lumen 1530 through wall portion 1520, where it would contact and solubilize the solid drug and/or functional agent payloads therein (not shown). This structure may be formed by co-extrusion, for example. The relative proportions of the two wall portions can be selected, for example, depending on the rate of (and thus surface area available for) water permeation and on the mechanical properties needed, for example, to give the device the flexibility/durometer values needed for transurethral insertion and bladder retention and tolerability, as described for example in U.S. Patent Application Publication No. 2011/0152839 to Cima et al.

Figure 18:
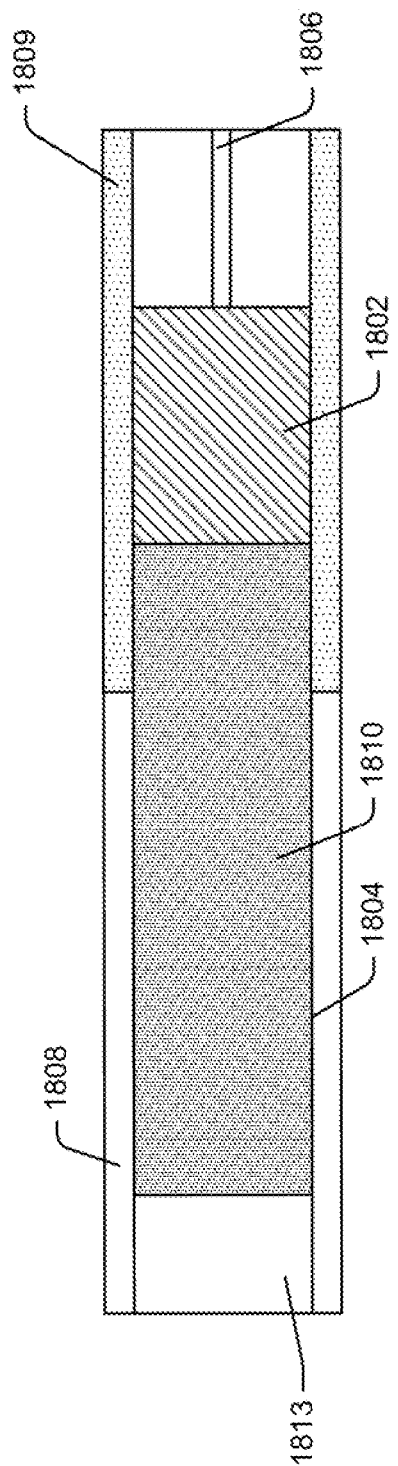
FIG. 18 is a cross-sectional view of one embodiment of a multi-unit drug delivery device.

As shown in FIG. 18, the drug delivery device 1800 may include a water impermeable coating region 1809 along at least a portion of tubular housing 1808. That is, a water impermeable wall portion may be formed by coating the housing with a water impermeable material. For example, osmotic tablets 1810 and drug tablets 1802 may be contained in reservoir 1804, which is bounded by a sealed end 1813 and a release orifice plug 1806. Upon insertion into the patient, water permeates into reservoir 1804 through water permeable housing 1808 (but not through water impermeable region 1809), where it contacts and solubilizes the functional agent and drug tablet payloads therein. The water impermeable region allows for the controlled solubilization and release of the drug. In particular, a housing coating may be useful for osmotic release devices where the housing material is permeable to the drug.

For example, a water impermeable coating region may extend along from 4 cm to 11 cm of the housing length, such as 6.5 cm along the housing length. In certain embodiments, a tubular housing has an inner diameter of 2.64 mm, and contains 6 to 11 cm of functional agent tablets and 2 to 4.5 cm of drug tablets, while having an impermeable coating region extending from 4 cm to 11 cm of the housing length. For example, a water impermeable parylene coating may be provided on a silicone or other housing.

As mentioned above, the wall of the device housing may have one or more passageways through its surface, providing a path for water flow into and/or drug flow from the reservoir. In some embodiments, the wall may be porous, meaning the wall may have one or more passing pores formed therein. In other embodiments, the wall may in the form of a defined aperture formed completely through the wall, such as by drilling, punching, or molding. The aperture may have a circular or other shape. The aperture may have a straight or tapered sidewall extending through the wall.

In some embodiments, the wall is made of an elastic, biocompatible polymeric material. The material may be non-resorbable or resorbable. Example non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, and poly(siloxanes). Example resorbable materials, specifically biodegradable or bioerodible polymers, include synthetic polymers selected from poly(amides), poly(esters), poly (ester amides), poly(anhydrides), poly(orthoesters), polyphosphazenes, pseudo poly(amino acids), poly(glycerol-sebacate), poly(lactic acids), poly(glycolic acids), poly(lactic-co-glycolic acids), poly(caprolactones), poly(caprolactone) (PC) derivatives, amino alcohol-based poly(ester amides) (PEA) and poly (octane-diol citrate) (POC), and other curable bioresorbable elastomers. PC-based polymers may require additional cross-linking agents such as lysine diisocyanate or 2,2-bis($\varepsilon$-caprolacton-4-yl)propane to obtain elastomeric properties. Copolymers, mixtures, and combinations of the above materials also may be employed.

In certain embodiments, the housing may be formed from a material that is both water-permeable and flexible. Silicone is one example polymeric material that is flexible and can act as a water-permeable membrane when formed as a thin wall, with the permeability determined at least in part by the wall thickness. For example, a thin wall of silicone may have a thickness in the range of about 100 µm to about 1000 µm, although other wall thickness can be used. Further, a thin wall of silicone may be permeable to some drugs, depending on, for example, the porosity of the wall, the size of the drug molecule, its molecular weight, or its charge.

The size of the housing, including the thickness of the wall, may be selected based on the volume of drug and functional agent formulations to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device and/or may not have sufficient flexibility to permit delivery through a urethra or other narrow body lumen.

For example, the housing may be an elongated, annular tube having an inner diameter from about 2 mm to about 5 mm. The first and second units may be solid tablets having a diameter substantially the same as the inner diameter of the elongated annular tube. One or more of the first unit tablets may fill a length from about 1 cm to about 3 cm of the lumen of the tube, and one or more of the second unit tablets may fill a length from about 10 cm to about 15 cm of the lumen of the tube. In one embodiment, the ratio of volume of the first unit(s) to volume of the second unit(s) is from about 0.05 to about 0.5. Other lengths and ratios of the tablet payloads are envisioned.

For example, the housing may be an elongated, annular tube having a wall thickness from 0.1 to 0.4 mm, such as a wall thickness of 0.2 mm. The housing material may be selected such that the housing has a durometer from 25 A to 80 A, such as 25 A, 50 A, 65 A, 70 A, or 80 A.

In certain embodiments, the device is elastically deformable between a relatively straightened shape suited for insertion through the urethra of a patient and into the patient's bladder and a retention shape suited to retain the device within the bladder. For example, the device may include a retention frame lumen having a retention frame positioned therein. The retention frame may be made of a superelastic alloy or other elastic wire, as described in U.S. Patent Application Publication No. 2010/0331770 to Lee et al., which is incorporated herein by reference.

An example embodiment is shown in FIG. 5, wherein the device 500 includes a housing 508 that houses the first and second units 502, 510, and a retention frame 512. The drug housing 508 is axially aligned with the retention frame 512, and is formed from a flexible material, which permits moving the device 500 between the retention shape shown in FIG. 5, and a straightened deployment shape, such as shown in FIG. 3. "Retention shape" generally denotes any shape suited for retaining the device in the intended implantation location, including but not limited to the pretzel-like shape shown in FIG. 5 that is suited for retaining the device in the bladder, while "deployment shape" generally denotes any shape suited for deploying the drug delivery device into the body, including the linear or elongated shape shown in FIG. 3 that is suited for deploying the device through a working channel of a deployment instrument positioned in the urethra or other natural lumen. In one embodiment, the device is configured to spontaneously assume a shape having an interconnected and overlapping pair of coils, in the absence of a compressive load, such as caused by being forced into a deployment shape and/or through a deployment instrument.

Figure 16:
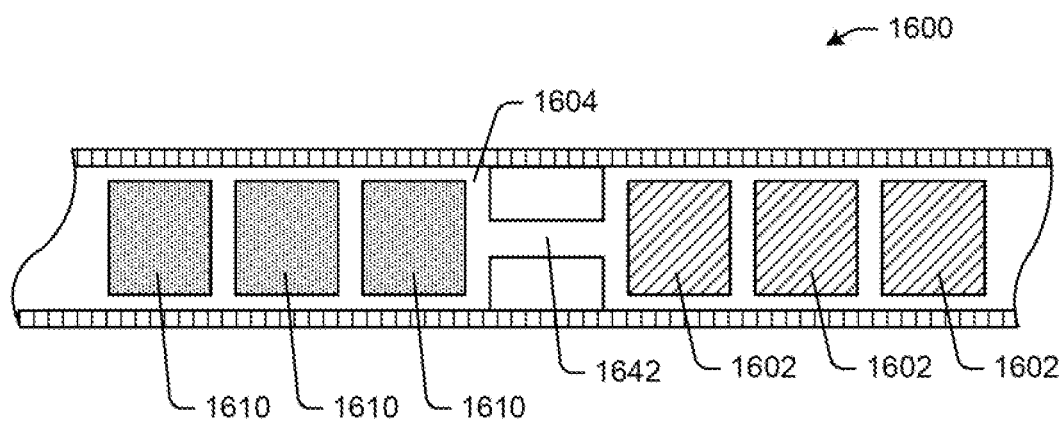
FIG. 16 is a cross-sectional view of one embodiment of a drug delivery device in which the reservoir includes a flow channel modulator.

In certain embodiments, as shown in FIG. 16, the reservoir 1604 of the device 1600 includes a flow modulator channel 1642 positioned between the first and second units 1602, 1610. For example, the flow modulator channel may be a passage having a diameter smaller than the reservoir's diameter. The flow modulator channel may serve to limit the flow between channels (i.e. reservoir sections), and thus slow down the release of drug from the housing by limiting the ability of the functional agent to contact the drug. In certain embodiments, the device may include more than one flow modulator channel for further control of the rate of drug release from the device.

In certain embodiments, a drug delivery device includes a first housing portion loaded with a drug formulation, and a second housing portion loaded with an excipient, and is configured to release the drug according to a first release profile and is configured to release the excipient according to a second release profile which differs from the first release profile. The housing portions may achieve different release rates by having different configurations, by housing different formulations, or by employing different release mechanisms, among others, or combinations thereof. The housing portions may be combined to achieve a desired drug release profile. For example, the excipient may be a functional agent configured to facilitate release and/or delivery of the drug, such as a drug solubilizing agent, a drug stabilizing agent, or a permeation enhancing agent. The drug formulation and/or the excipient may be in the form of one or more tablets.

For example, the device may include housing portions that exhibit different induction or lag times before the onset of initial release, that release the drug and excipient at different rates or according to different release curves after the onset of release, or that release the drug and excipient for different periods before the payloads are substantially exhausted, among others or combinations thereof. The disparate housing portions may be combined to achieve a desired release profile from the drug delivery device as a whole, such as a release profile that demonstrates a relatively short initial lag time and thereafter demonstrates continued release at a relatively constant rate over an extended period.

For example, the drug and excipient may be released by osmotic pumping or diffusion, as described above, or some combination thereof. In certain embodiments, the drug is released from the first housing portion, through an aperture in the first housing portion, primarily via osmotic pressure, and the excipient is released from the second housing portion by diffusion. In another embodiment, the drug is released from the first housing portion by diffusion through a drug permeable wall in the first housing portion, and the excipient is released from the second housing portion, through an aperture in the second housing portion, primarily via osmotic pressure.

Figure 7:
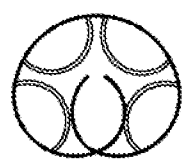
FIG. 7 illustrates example configurations for drug delivery devices having more than one drug housing portion.
Figure 7:
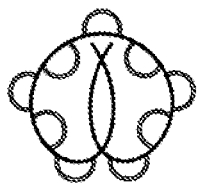
Figure 7:
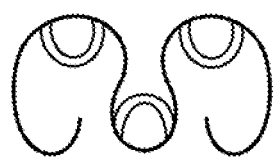
Figure 7:
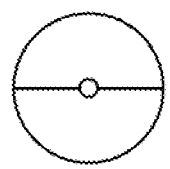
Figure 7:
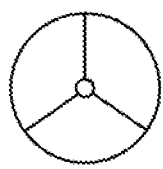
Figure 7:
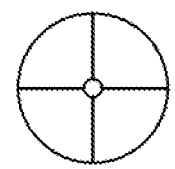
Figure 7:
Figure 7:
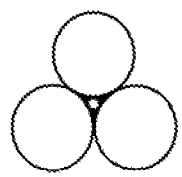
Figure 7:
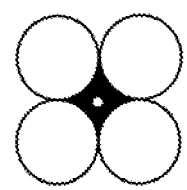

In particular embodiments, the drug delivery device includes at least two discrete or segregated housing portions associated with a single retention portion. The housing portions may be separate reservoir housings each associated with the retention portion, or the housing portions may be separate areas within a single housing that is associated with the retention portion. FIG. 7 illustrates example housing portions with separate reservoir housings in Examples A through C. FIG. 7 also illustrates example housing portions that are segregated areas within a single housing in Examples D through F. FIG. 7 also illustrates housing portions in Examples G through I that could have either configuration depending on materials and construction.

Figure 8:
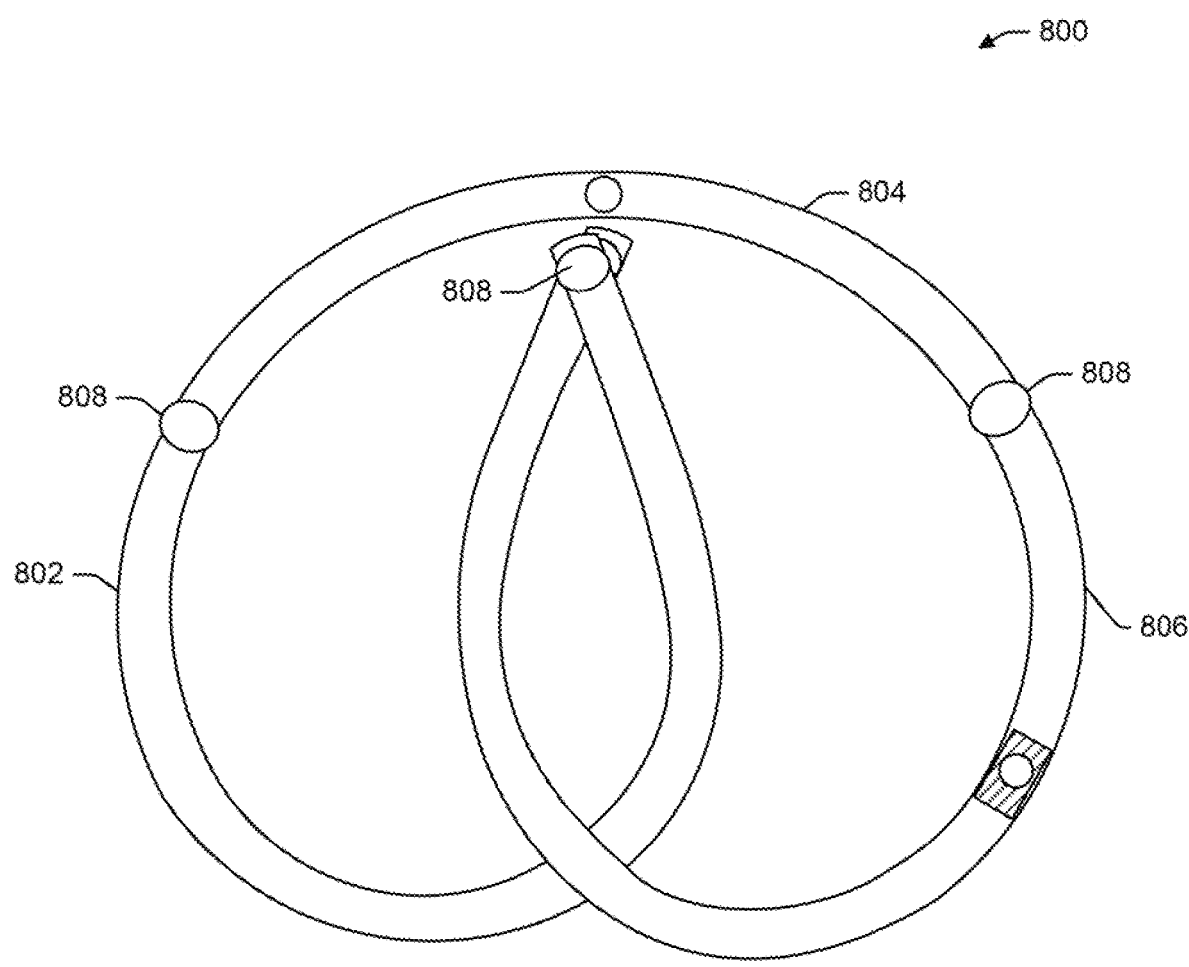
FIG. 8 is a plan view of an embodiment of a drug delivery device having more than one drug housing portion.

FIG. 8 is a plan view of another embodiment of a drug delivery device 800 having a housing that is partitioned into multiple segregated housing portions. Three housing portions 802, 804, and 806 are shown, although any number may be used. Each housing portion is defined by a portion of the wall of the housing and at least one partition structure 808, which separates the housing portion from an adjacent housing portion. The partition structure 808 may be a plug inserted into the housing, such as a cylinder, sphere, or disk, among others, which is secured in place due to its size or with an adhesive. The partition structure 808 also may be a portion of the housing formed directly therein, such as by molding. For example, the webs shown in Examples D through E of FIG. 7 are partition structures that segregate housing portions along the length of the device.

A device with at least two discrete housing portions may be suited for controlled release of at least one drug payload and at least one excipient or functional agent payload from a corresponding number of reservoirs. The two discrete portions may have the same configurations or different configurations, such one or any combination of the configurations described above with reference to FIGS. 1-6. Configurations of drug delivery devices having two distinct drug portions are further described in U.S. Application Publication No. 2011/0060309 to Lee et al.

II. Use and Applications of Implantable Drug Delivery Devices

The implantable drug delivery devices described herein can be used in a variety of medical applications, particularly therapeutic and prophylactic treatments for patients. In certain embodiments, the device is configured to deliver a drug such as lidocaine, gemcitabine, docetaxel, carboplatin, cisplatin, oxaliplatin, trospium, tolterodine, or mitomycin C.

In some embodiments, the devices provide pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, and naproxen.

In embodiments, the drug delivery device is used to treat inflammatory conditions such as interstitial cystitis, chemical cystitis, radiation cystitis, hemorrhagic cystitis induced by radiation and chemotherapy, ketamine cystitis (or ketamine bladder syndrome), painful bladder syndrome, prostatitis, urethritis, post-surgical pain, and kidney stones. Non-limiting examples of specific drugs for these conditions include lidocaine, immunosuppressive agents (e.g., tacrolimus, liposomal tacrolimus), glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote stone dissolution.

In some embodiments, the drug delivery device is used in association with the placement of a ureteral stent, such as to treat pain, urinary urgency or urinary frequency resulting from ureteral stent placement. Non-limiting examples of specific drugs for such treatment include anti-muscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In other embodiments, the drug delivery device is used to treat urinary tract cancer, such as bladder cancer, or prostate cancer. Drugs that may be used include antiproliferative agents, cytotoxic agents, chemotherapeutic agents, or a combination thereof. Representative examples of drugs which may be suitable for the treatment of urinary tract cancer include *Bacillus* Calmette Guerin (BCG) vaccine, docetaxel, oxaliplatin, carboplatin, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, histone deacetylase inhibitors (e.g. suberoylanilide hydroxamic acid) and cyclophosphamide. The drug may be a biologic, and it may include a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. The drug treatment may be coupled with a conventional radiation or surgical therapy targeted to the cancerous tissue.

In still other embodiments, the device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

Drugs for the treatment of neurogenic bladder may be categorized into one of two general types: those for treating spastic neurogenic bladder and those for treating flaccid neurogenic bladder. In embodiments, the drug is selected from those known for the treatment of incontinence due to neurologic detrusor overactivity and/or low compliant detrusor. Examples include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In other embodiments, the drug is selected from those known for the treatment of incontinence due to neurologic sphincter deficiency. Examples include alpha adrenergic agonists, estrogens, beta-adrenergic agonists, tricyclic antidepressants (imipramine, amitriptyline). In still other embodiments, the drug is selected from those known for facilitating bladder emptying (e.g., alpha adrenergic antagonists (phentolamine) or cholinergics). In yet other embodiments, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinic agonist, choline ester).

In certain embodiments, functional agents or excipients include osmotic agents, drug solubilizing agents, drug stabilizing agents, permeation enhancing agents, or combinations thereof. In particular, the functional agents or excipients may be suited to facilitate in vivo release or delivery of the drug to the implantation site. For example, the drug may be a low solubility drug and the functional agent may be an osmotic agent, such as urea. Upon solubilization, the osmotic agent may facilitate release of the drug from the housing by fluid flow induced by osmotic pressure. Other examples of functional agents and excipients that may be used include cyclodextrins, glycerol, polyethylene glycol, citrates, acetates, phosphates, ascorbic acid, and sodium sulfite.

In embodiments, the first unit(s) contains a high weight percentage of drug, and the second unit(s) contains a high weight percentage of functional agent or excipient. For example, the first unit may contain at least 50 percent by weight drug, at least 60 percent by weight drug, at least 75 percent by weight drug, from about 60 to about 99 percent by weight drug, or from about 75 to about 95 percent by weight drug. The second unit may contain at least 80 percent by weight functional agent, at least 85 percent by weight functional agent, at least 90 percent by weight functional agent, from about 80 to about 99 percent by weight functional agent, or from about 85 to about 95 percent by weight functional agent. The remainder of the units may include excipients such as pharmaceutical lubricants, stabilizing agents, or binding agents, for example oil-based lubricants, PEG, or PVP. The excipients may also include a release delay agent. For example, a release delay agent could be provided in a portion of the drug units, a portion of the functional agent units, or both to further control release of the drug.

In a particular embodiment, the first unit contains at least 75 percent by weight gemcitabine HCl, and the second unit contains at least 85 percent by weight urea. For example, the first unit may contain about 80 percent by weight gemcitabine HCl, and the second unit may contain about 90 percent by weight urea.

In one embodiment, the housing is water permeable, the first unit includes a first tablet that contains a low solubility drug, and the second unit includes a second tablet that contains an osmotic agent that facilitates release of the drug from the housing by osmotic pressure. In one embodiment, the drug is gemcitabine and the osmotic agent is urea.

The device may be inserted in a body cavity or lumen of the patient. Once implanted, the device may release one or more drugs for the treatment of one or more conditions, either locally to one or more tissues at the deployment site, regionally to other tissues distal from the deployment site, or both. The release may be controlled over an extended period. Thereafter, the device may be removed, resorbed, excreted, or a combination thereof.

In certain embodiments, the device is inserted into a patient by passing the device through a deployment instrument and releasing the device from the deployment instrument into the body. The deployment instrument may be any suitable lumen device, such as a catheter, a urethral catheter, a cystoscope, or a combination thereof, whether commercially available or specially adapted for deploying the present device. In particular embodiments, the device is implanted in the bladder. The device is then retained in the bladder due to the retention feature, such as by assuming a retention shape or anchoring in the bladder.

The device may be deployed in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

Following in vivo deployment, the device releases the drug. Release may occur, as described above, due to an osmotic pressure gradient between the interior and exterior of the device, the drug passing through one or more orifices or passing pores in the device under the force of osmotic pressure. Release may also occur by diffusion, whereby the drug passes through one or more orifices or passing pores in the device and/or through a drug-permeable wall of the device, due to a drug concentration gradient between the interior and exterior of the device. Combinations of these release modes within a single device are possible, and in some embodiments are preferred in order to achieve an overall drug release profile not readily achievable from either mode individually.

Following insertion of the device into the patient, water or aqueous bodily fluid from the implantation site may enter the device, such as through a water-permeable wall or a passageway in the wall of the device, to solubilize the functional agent or excipient and the drug. For example, the functional agent and drug may be solubilized upon contact with urine in cases in which the device is implanted in the bladder. The functional agent may be a solubilizing agent configured to facilitate solubilization of the drug.

In particular embodiments, release of at least two payloads (i.e., one drug payload and one excipient and/or functional agent payload) may occur in accordance with different release profiles, including profiles that exhibit different initial onsets of release, such as immediate and delayed release; profiles that exhibit different durations of release, such as quick and extended release; and profiles that exhibit different release rates, whether a zero-order release rate or otherwise. Continuous and extended release is thus facilitated in accordance with a desired profile. For example, the device may release a functional agent payload relatively quickly, and the device may release a drug payload more continuously.

The device may provide extended, continuous, intermittent, or periodic release of a desired quantity of drug over a desired, predetermined period. In various embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated. In embodiments, the device is configured to release a therapeutically effective amount of the drug over a period from 1 day to 30 days, such as from 2 days to 30 days, from 1 day to 21 days, from 1 day to 14 days, from 2 days to 14 days, or from 5 days to 7 days, etc. In certain embodiments, the drug is released from the device at a zero order rate over a period from 1 day to 30 days, such as from 2 days to 14 days, or from 3 days to 7 days.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination, as described for example in U.S. Patent Application Publication No. 2012/0089122 to Lee et al., which is incorporated herein by reference. The device may not be retrieved or resorbed until some of the drug, or preferably most or all of the drug, has been released. If needed, a new drug-loaded device may subsequently be implanted, during the same procedure as the retrieval or at a later time.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more. In such cases, the device may be used to treat interstitial cystitis, chemical cystitis, radiation cystitis, hemorrhagic cystitis induced by radiation and chemotherapy, ketamine cystitis (or ketamine bladder syndrome), pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof.

In some embodiments, the drug delivery device is deployed into the bladder of a patient for regional drug delivery to one or more nearby genitourinary sites. The device may release drug locally to the bladder and regionally to other sites near the bladder. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions. Such delivery may provide an alternative to systemic administration, which may entail undesirable side effects or result in insufficient bioavailability of the drug.

The present invention may be further understood with reference to the following non-limiting examples. Unless indicated otherwise, all percentages are weight percentages.

Example 1

Single Unit Versus Multi-Unit Devices

Drug delivery device models were prepared using silicone tubing having an inner diameter of 2.64 mm.

A single unit device was prepared, in accordance with the device embodiment shown in FIG. 1. The tube was loaded with a plurality of tablets containing 17.7 percent gemcitabine hydrochloride (164 mg FBE), 73.6 percent urea, 7.8 percent of oil-based pharmaceutical lubricant LUBRITAB® (commercially available from JRS PHARMA, Rosenberg, Germany), and 0.9 percent polyvinylpyrrolidone (PVP) K29-32 (commercially available as PLASDONE® from International Specialty Products, New Jersey). The tablets were formed to have a diameter substantially the same as the inner diameter of the tube, and were loaded into the tube in a serial arrangement. The tablets filled a length of 15.2 cm. The device included a spacer-type release orifice with a length of 5 mm.

A multi-unit device was also prepared, in accordance with the device embodiment shown in FIG. 2. The tube was loaded with a plurality of drug tablets containing 80.0 percent gemcitabine HCl, 13.3 percent urea, 4.2 percent PVP K29-32, and 2.5 percent polyethylene glycol (PEG) 8000. The drug tablets filled a length of 2.8 cm and were serially positioned adjacent a spacer-type release orifice with a length of 5 mm. The tube was also loaded with a plurality of functional agent tablets containing 90.0 percent urea and 10.0 percent oil-based pharmaceutical lubricant LUBRITAB®. The functional agent tablets filled a length of 12.0 cm of the tube.

The total formulation of the multi-unit device was 18.9 percent gemcitabine HCl, 71.8 percent urea, 7.7 percent oil-based pharmaceutical lubricant LUBRITAB®, 1.0 percent PVP K29-32, and 0.6 percent PEG 8000, which was comparable to the total formulation of the single unit device. In particular, the single unit device contained 164.0 mg gemcitabine FBE, while the multi-unit device contained 163.8 mg gemcitabine FBE.

Figure 9:
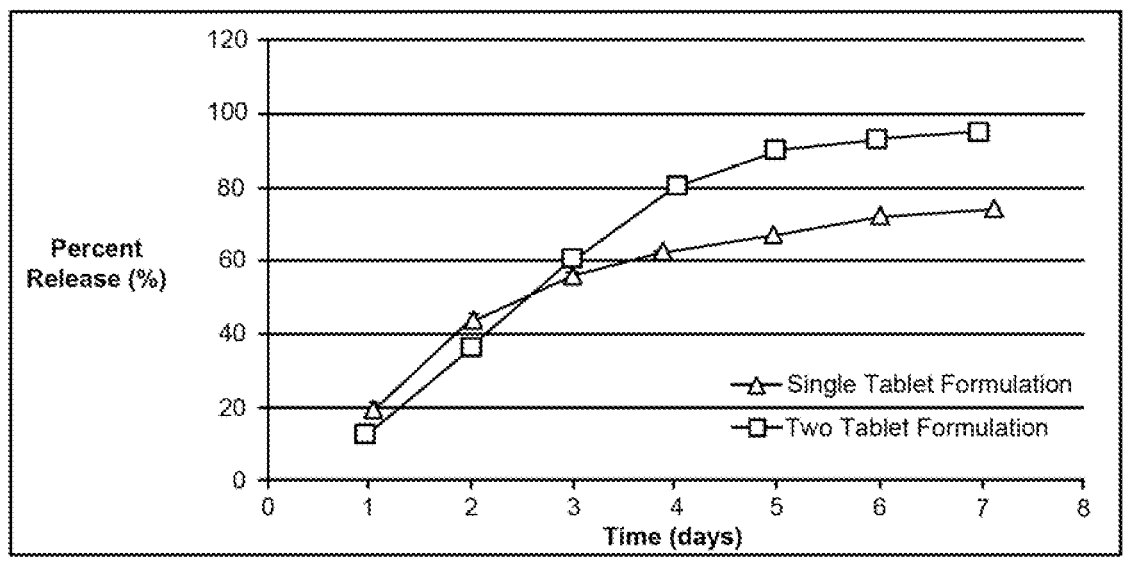
FIG. 9 is a graph showing the percent drug release over time of a single tablet drug delivery device and a two tablet drug delivery device.
Figure 10:
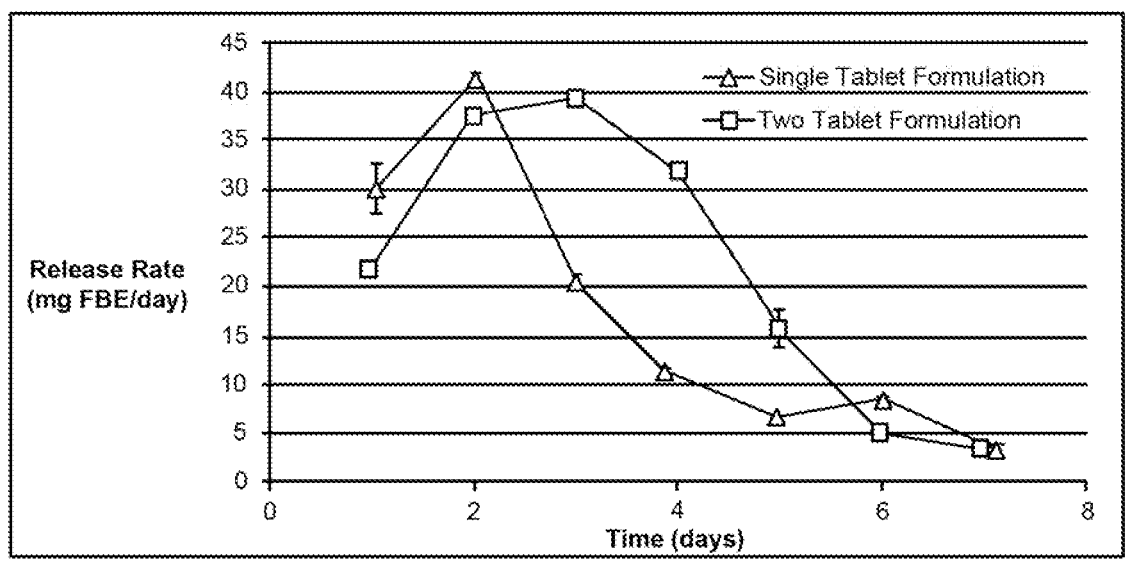
FIG. 10 is a graph showing the drug release rate over time of a single tablet drug delivery device and a two tablet drug delivery device.

The in vitro drug release profiles were measured for both the single unit and multi-unit devices in water. FIGS. 9 and 10 show the percent drug release and release rate (measured in mg gemcitabine FBE per day) versus time, respectively. Overall, the multi-unit device performed better than the single unit device, releasing a higher percentage of the drug, and maintaining a higher release rate of the drug for a longer period. As shown in FIG. 9, the multi-unit device released over 90 percent of its drug payload in a 7 day period, while the single unit device released less than 80 percent of its drug payload in the same period. As shown in FIG. 10, the multi-unit device also had a "flatter" release profile in which the drug release rate plateaued between days 2 and 4. A flat profile is desirable for extended release of the drug. For example, the multi-unit device performs much better than the single unit device at continuous, extended drug release over 5 to 7 days.

Example 2

Laser Drilled Versus Spacer-Type Release Orifices in Multi-Unit Devices

A multi-unit device having a spacer-type release orifice was prepared, in accordance with the device embodiment shown in FIG. 2. The release orifice had a length of 5 mm and an inner diameter of 0.3 mm. The spacer orifice was located at one end of the tube.

A multi-unit device having a laser drilled release orifice was prepared, in accordance with the device embodiment shown in FIG. 3. The release orifice had an inner diameter of 0.150 mm and was located in the housing wall of the device.

Each tube was filled with a plurality of drug tablets and a plurality of functional agent tablets. The functional agent tablets contained 90.0 percent urea and 10.0 percent oil-based pharmaceutical lubricant LUBRITAB®, and filled a tube length of 6.0 cm. The drug tablets contained 80.0 percent gemcitabine HCl, 13.3 percent urea, 4.2 percent PVP K29-32, and 2.5 percent polyethylene glycol (PEG) 8000, and filled a tube length of 2.5 cm. The laser-drilled device contained 141.6 mg gemcitabine FBE, and the spacer orifice device contained 140.5 mg gemcitabine FBE).

As shown in FIG. 3, in the laser drilled orifice device 300, 3 cm of functional agent tablets 310 were located on each side of 2.5 cm of drug tablets 302, such that the drug tablets 302 were centered about the laser drilled orifice 306. As shown in FIG. 2, in the spacer orifice device 200, 2.5 cm of the drug tablets 202 were located adjacent the spacer orifice 206, and 6.0 cm of functional agent tablets 210 were located adjacent the drug tablets 202.

Figure 11:
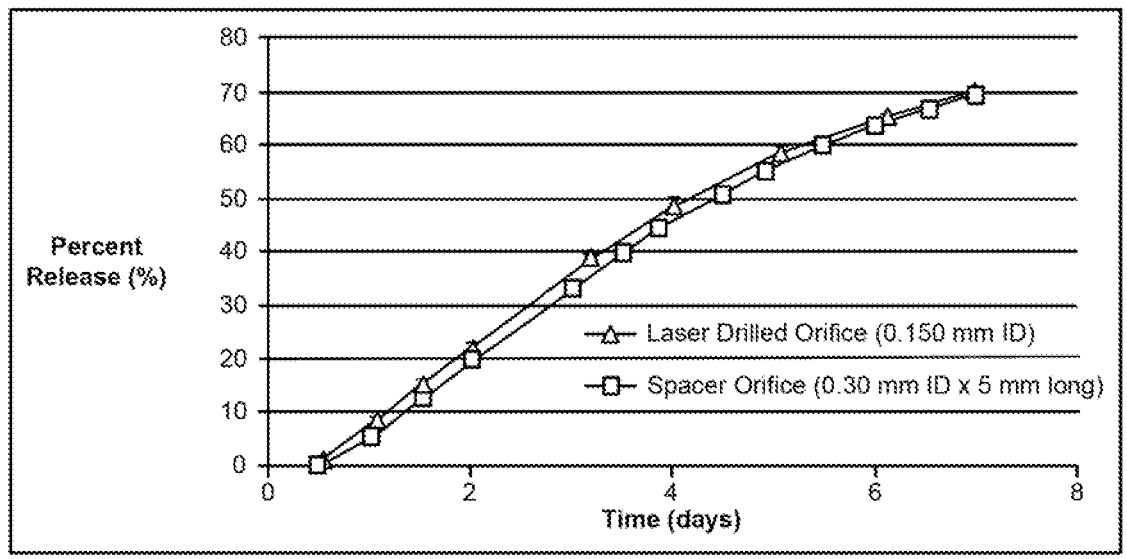
FIG. 11 is a graph showing the percent drug release over time of a drug delivery device having a laser drilled orifice and a drug delivery device having a spacer orifice.
Figure 12:
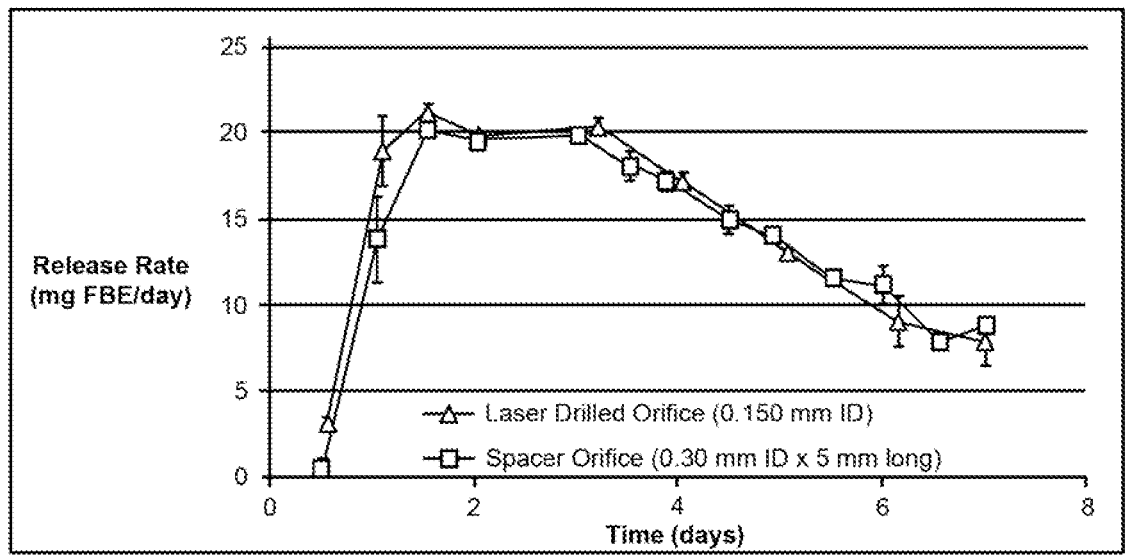
FIG. 12 is a graph showing the drug release rate over time of a drug delivery device having a laser drilled orifice and a drug delivery device having a spacer orifice.

The in vitro drug release profiles were measured for both the laser drilled orifice and spacer orifice devices in water. FIGS. 11 and 12 show the percent drug release and release rate (measured in mg FBE gemcitabine per day) versus time, respectively. Generally, both devices displayed similar release profiles, releasing up to about 70 percent of the drug payload over 7 days at a substantially zero-order rate. The release rate profiles of the devices are also similar, with a plateau region at about 20 mg FBE/day release between days 1 to 4.

Example 3

Powdered Drug Versus Tablet Drug Multi-Unit Devices

A multi-unit device having drug tablets and functional agent tablets was prepared, in accordance with the device embodiment shown in FIG. 2. The functional agent tablets contained 90.0 percent urea and 10.0 percent oil-based pharmaceutical lubricant LUBRITAB® and filled a tube length of 6.0 cm. The drug tablets contained 80.0 percent gemcitabine HCl, 13.3 percent urea, 4.2 percent PVP K29-32, and 2.5 percent polyethylene glycol (PEG) 8000, and filled a tube length of 1.5 cm. The tablet drug device contained 123.4 mg gemcitabine FBE.

A multi-unit device having functional agent tablets and a powdered drug unit was prepared, in accordance with the device embodiment shown in FIG. 4. The functional agent tablets 410 contained 80 percent urea and 20 percent oil-based pharmaceutical lubricant LUBRITAB®, and filled a tube length of 7.8 cm. The drug powder unit 402 contained 80 percent gemcitabine HCl and 20 percent urea powder, and filled a tube length of 3.4 cm. The powdered drug device contained 124.4 mg gemcitabine FBE.

Each device included a spacer-type release orifice having an inner diameter of 0.300 mm and a length of 5.0 mm.

Figure 13:
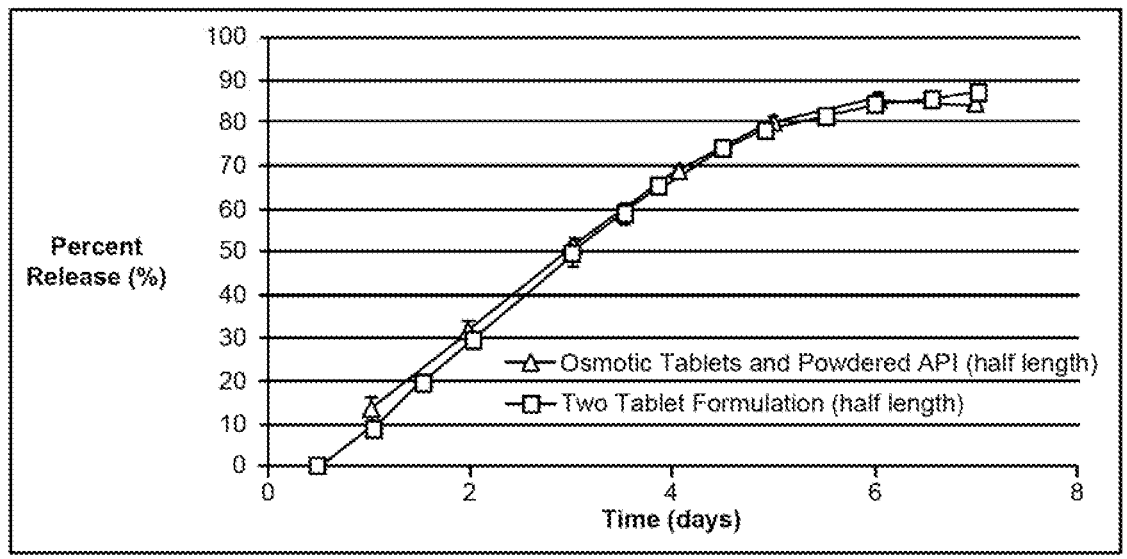
FIG. 13 is a graph showing the percent drug release over time of a drug delivery device containing a powdered drug and an osmotic agent tablet, and a drug delivery device containing a drug tablet and an osmotic agent tablet.
Figure 14:
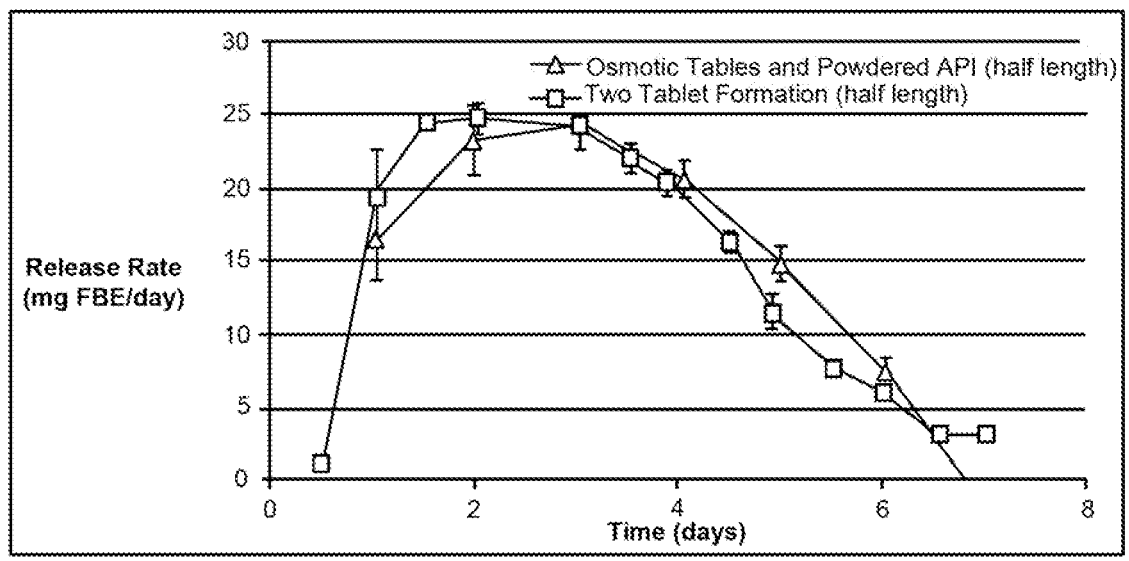
FIG. 14 is a graph showing the drug release rate over time of a drug delivery device containing a powdered drug and an osmotic agent tablet, and a drug delivery device containing a drug tablet and an osmotic agent tablet.

The in vitro drug release profiles were measured for both the laser drilled orifice and spacer orifice devices in water. FIGS. 13 and 14 show the percent drug release and release rate (measured in mg FBE gemcitabine per day) versus time, respectively. Generally, both devices displayed similar release profiles, releasing up to about 85 percent of the drug payload over 7 days at a substantially zero-order rate. The release rate profiles of the devices are also similar, with a plateau region above 20 mg FBE/day release between days 1 to 4.

As can be seen from the above Examples, multi-unit drug delivery devices provide improvements to both the short and long-term drug release profiles compared to comparable single unit devices. These devices advantageously allow for controlled, extended drug release, for example zero-order release over 5 to 7 days. Moreover, these devices provide a means for delivering low solubility drugs to patients via osmotic release devices. This is especially useful for drugs that are difficult to reformulate into more highly soluble forms. Thus, these devices are able to deliver a variety of drugs via various release mechanisms and release kinetics profiles, and provide enhanced control of drug release in vivo, for example from a device deployed in the bladder.

Example 4

Effect of Wall Thickness and Durometer of Silicone Tube Housing on Drug Release from Device A multi-unit device having drug tablets and functional agent tablets was prepared, in accordance with the device embodiment shown in FIG. 17. The functional agent tablets were osmotic tablets. The osmotic tablet mass and length were approximately 400 mg and 6 cm, respectively, and the drug tablet mass and length were approximately 150 mg and 2 cm, respectively. The drug (gemcitabine) tablet formulation was 85.5 percent gemcitabine HCl, 5 percent urea, 4.5 percent PVP K30, 2.5 percent synthetic magnesium aluminometasilicate excipient NEUSILIN®, and 2.5 percent magnesium stearate. The osmotic tablet formulation was 90 percent urea and 10 percent oil-based pharmaceutical lubricant LUBRITAB®. All tablets were made by direct powder compaction method.

Four different kinds of extruded silicone tubular housings were used in this example: 1) 2.64 mm inner diameter, 0.13 mm wall, 65 A Shore A durometer (MED-4765, NuSil Technology LLC); 2) 2.64 mm inner diameter, 0.1 mm wall, 80 A Shore A durometer (MED-4780, NuSil Technology LLC); 3) 2.64 mm inner diameter, 0.2 mm wall, 50 A Shore A durometer (MED-4750, NuSil Technology LLC); and 4) 2.64 mm inner diameter, 0.4 mm wall, 25 A Shore A durometer (MED-4720, NuSil Technology LLC).

Figure 19:
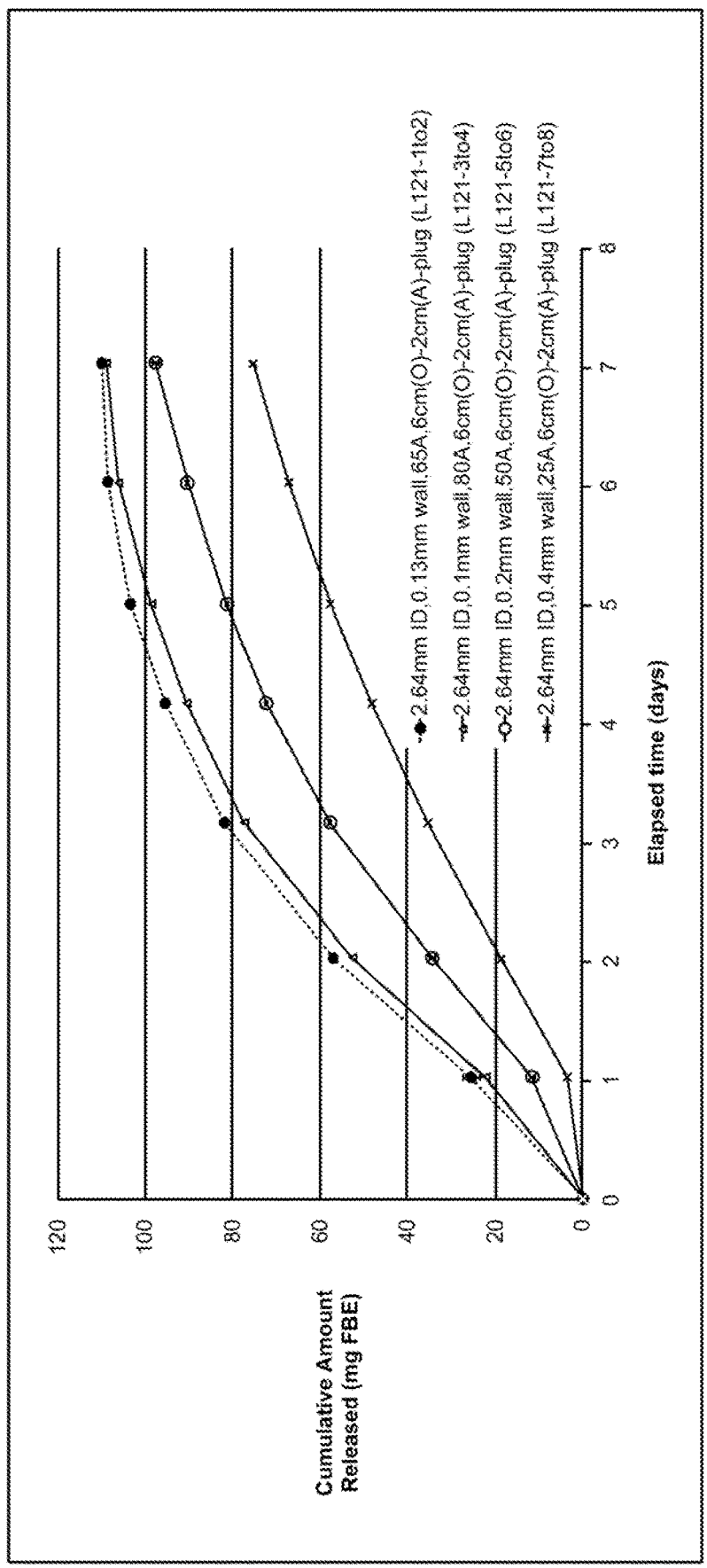
FIG. 19 is a graph showing the amount of drug released over time from drug delivery devices having various housing wall thickness and durometer.

In each device, as in FIG. 17, one end of the tube was sealed by silicone adhesive MED3-4213-1 (NuSil Technology LLC) and the other end included a restraining plug made from EVA support beading (FBK medical tubing), comprising Elvax 760, ethylene vinyl acetate (EVA) copolymer. The EVA plug had approximately 2.74 mm outer diameter and 5 mm length and a 30 to 60 degree cut was made at one end of the plug. The void space created by the cut surface and the silicone tube was filled with silicone adhesive, as shown in FIG. 17, which served as a stopper to prevent the detachment of the plug when osmotic pressure was built in the silicone tube. In vitro release was performed in deionized water at 37° C. and the results are shown in FIG. 19. The sample size for each group was 2 and the error bars indicate standard deviation (SD) around the mean. Some error bars are not seen if they are smaller than symbols. As used in the legend, "O" refers to osmotic tablet and "A" refers to active pharmaceutical ingredient, i.e., drug, tablet.

In particular, FIG. 19 shows the amount of drug released over time from the devices having various housing wall thickness and durometer. The performance of gemcitabine release was affected by the wall thickness and the durometer of the silicone tube housing. These results indicate that the size of the housing, including the thickness of the wall, and the hardness and flexibility of the housing material, may be selected based on the volume of drug and functional agent formulations to be contained as well as the desired rate of delivery of the drug from the tube.

Example 5

Effect of Wall Thickness and Durometer of Silicone Tube Housing on Drug Release from Device Another set of experiments was performed using the device configuration shown in FIG. 17. In this example, three different silicone tubular housings used were: 1) 2.64 mm inner diameter, 0.2 mm wall, 50 A Shore A durometer (MED-4750, NuSil Technology LLC); 2) 2.64 mm inner diameter, 0.2 mm wall, 70 A Shore A durometer (MED-4770, NuSil Technology LLC); and 3) 2.64 mm inner diameter, 0.4 mm wall, 25 A Shore A durometer (MED-4720, NuSil Technology LLC).

Figure 20:
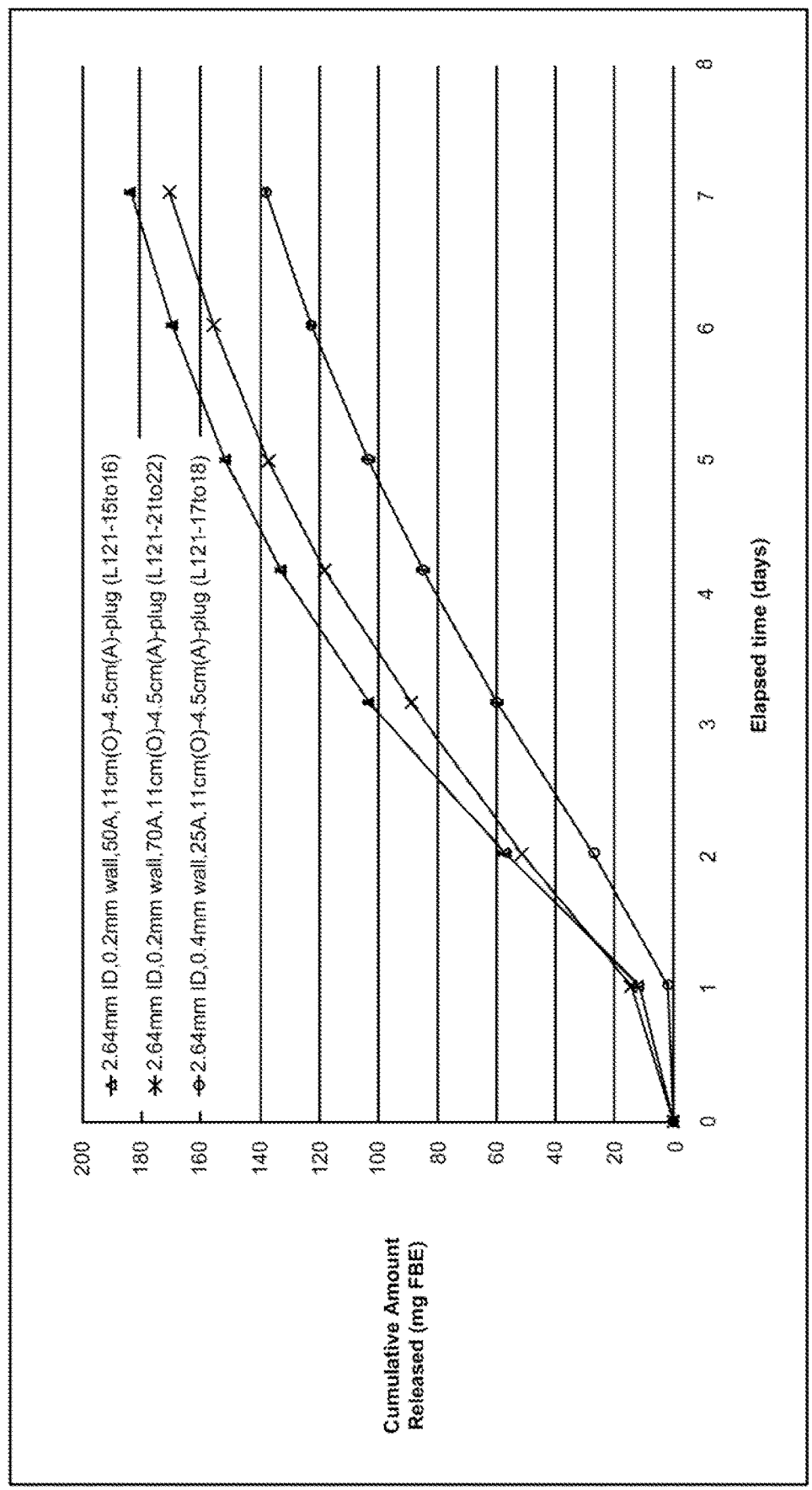
FIG. 20 is a graph showing the amount of drug released over time from drug delivery devices having various housing wall thickness and durometer.

The tablets were placed next to each other in the reservoir, as in FIG. 17. The osmotic tablet mass and length were approximately 700 mg and 11 cm, respectively, and the drug tablet mass and length were approximately 300 mg and 4.5 cm, respectively. The drug (gemcitabine) tablet formulation was 85.5 percent gemcitabine HCl, 5 percent urea, 4.5 percent PVP K30, 2.5 percent synthetic magnesium aluminometasilicate excipient NEUSILIN®, and 2.5 percent magnesium stearate. The osmotic tablet formulation was 90 percent urea and 10 percent oil-based pharmaceutical lubricant LUBRITAB®. All tablets were made by direct powder compaction method. In vitro release was performed in deionized water at 37° C. and the results are shown in FIG. 20. The sample size for each group was 2, and the error bars indicate standard deviation (SD) around the mean. Some error bars are not seen if they are smaller than symbols. As used in the legend, "O" refers to osmotic tablet and "A" refers to active pharmaceutical ingredient, i.e., drug, tablet.

In particular, FIG. 20 shows the amount of drug released over time from the devices having various housing wall thickness and durometer. The performance of gemcitabine release was affected by the wall thickness and the durometer of the silicone tube housing. These results indicate that the size of the housing, including the thickness of the wall, the length, and the hardness and flexibility of the housing material, may be selected based on the volume of drug and functional agent formulations to be contained as well as the desired rate of delivery of the drug from the tube.

Example 6

Effect of Length of Impermeable Coating Region of Silicone Tube Housing on Drug Release from Device A multi-unit device having drug tablets and functional agent tablets was prepared, in accordance with the device embodiment shown in FIG. 18. Unlike the earlier configurations, parylene C (a water impermeable coating) was partially coated on the extruded silicone tube having a 2.64 mm inner diameter, 0.2 mm wall, and 50 A Shore A durometer (MED-4750, NuSil Technology LLC). An orifice of 0.3 mm diameter was placed at one end of the tube while the other end was sealed by silicone adhesive MED3-4213-1. Three different configurations of the silicone tube housing were tested: 1) Osmotic tablet mass/length: 700 mg/11 cm, drug tablet mass/length: 320 mg/4.5 cm, parylene coated region length: 6.5 cm; 2) Osmotic tablet mass/length: 700 mg/11 cm, drug tablet mass/length: 320 mg/4.5 cm, parylene coated region length: 11 cm; and 3) Osmotic tablet mass/length: 400 mg/6 cm, drug tablet mass/length: 150 mg/2 cm, parylene coated region length: 4 cm.

Figure 21:
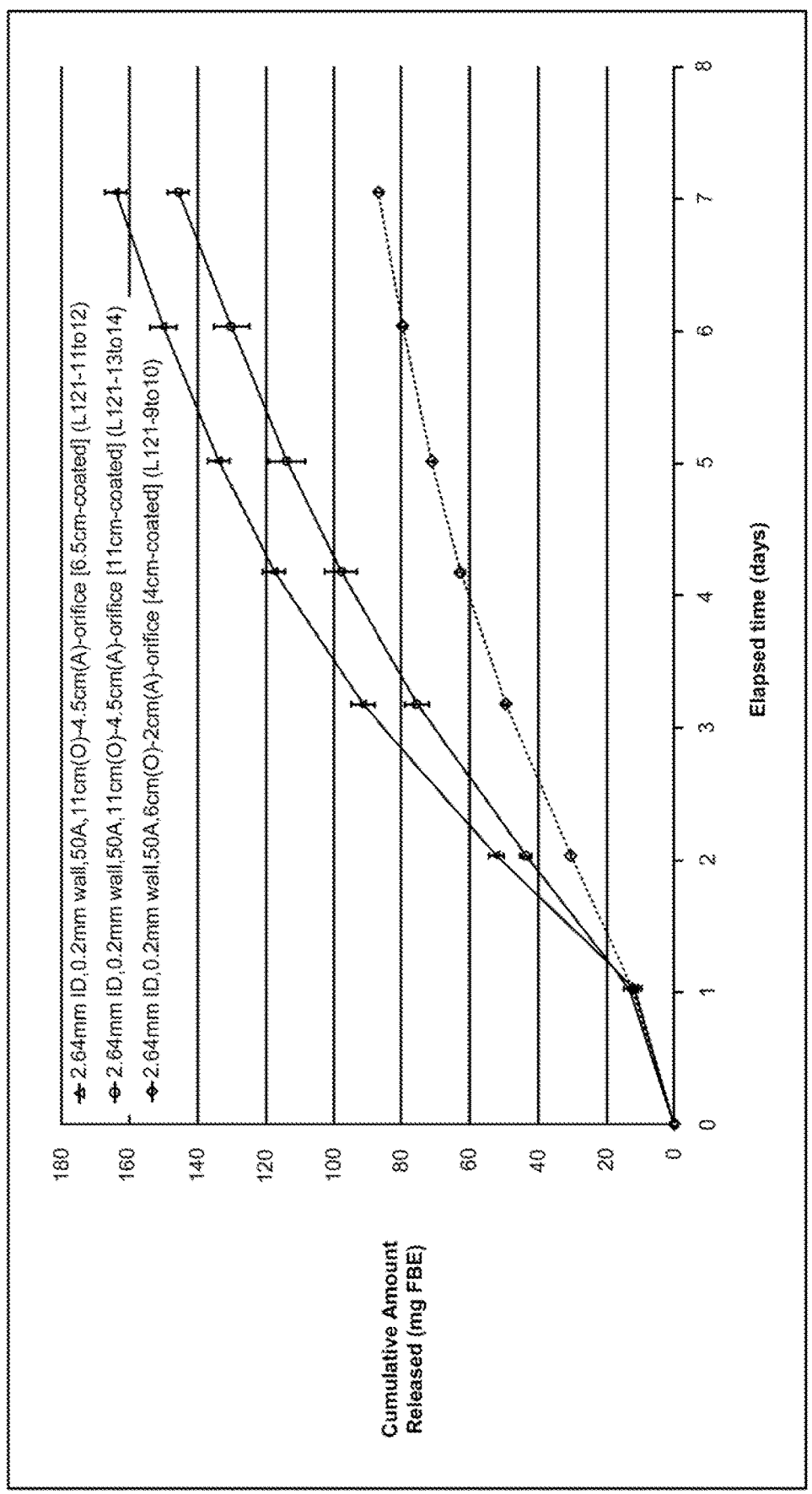
FIG. 21 is a graph showing the amount of drug released over time from drug delivery devices having a housing coating of various lengths.

In vitro release was performed in deionized water at 37° C. and the results are shown in FIG. 21. The sample size for each group was 2, and the error bars indicate standard deviation (SD) around the mean. Some error bars are not seen if they are smaller than symbols. As used in the legend, "O" refers to osmotic tablet and "A" refers to active pharmaceutical ingredient, i.e., drug, tablet.

In particular, FIG. 21 shows the amount of drug released over time from the devices having various water impermeable coating region lengths. The performance of gemcitabine release was affected by the length of parylene coated region relative to the lengths of osmotic and drug tablet regions. These results indicate that the length of the water impermeable region, may be selected based on the volume of drug and functional agent formulations to be contained as well as the desired rate of delivery of the drug from the tube. Moreover, a housing coating may be useful where the housing material is drug-permeable and osmotic release is desired.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An intravesical drug delivery device comprising:
a housing defining a reservoir, wherein the housing is an elongated, annular tube and the reservoir comprises an annulus of the annular tube;
a first unit contained within the reservoir in a first position, the first unit comprising a drug; and
a second unit contained within the reservoir in a second position distinct from the first position, the first position and the second position being in fluid communication with one another,
wherein the second unit comprises an osmotic agent that facilitates in vivo release of the drug from housing,
wherein the device is elastically deformable between a relatively straightened shape suited for insertion through the urethra of a patient and into the patient's bladder and a retention shape suited to retain the device within the bladder,
wherein a drug release orifice is provided in (i) an end plug located at an end of the tube, or (ii) a sidewall of the tube, and
wherein the first unit is located closer than the second unit to the drug release orifice.

2. The device of claim 1, wherein the housing comprises a water permeable wall portion defining at least part of the reservoir.

3. The device of claim 2, wherein the water permeable wall portion is substantially impermeable to the drug in aqueous solution.

4. The device of claim 1, wherein the drug is a low solubility drug.

5. The device of claim 1, wherein the first unit or the second unit is in the form of one or more solid tablets, or wherein the first unit and the second unit each are in the form of one or more solid tablets.

6. The device of claim 1, wherein the housing is an elongated annular tube, the annular tube comprising a water permeable wall portion and a water impermeable wall portion.

7. The device of claim 6, wherein the water impermeable wall portion comprises a water impermeable coating.

8. The device of claim 1, wherein the housing is an elongated, annular tube having a wall thickness from 0.1 to 0.4 mm.

9. The device of claim 1, wherein the housing has a durometer from 25 A to 80 A.

10. The device of claim 1, wherein the housing comprises silicone, a thermoplastic polyurethane, ethylene-co-vinyl acetate (EVA), or a combination thereof.

11. The device of claim 1, wherein the drug comprises lidocaine, gemcitabine, docetaxel, carboplatin, cisplatin, oxaliplatin, trospium, tolterodine, or mitomycin C.

12. The device of claim 1, wherein the drug comprises gemcitabine and the osmotic agent comprises urea.

13. The device of claim 12, wherein the first unit comprises at least 75 percent by weight gemcitabine HCl and the second unit comprises at least 85 percent by weight urea.

14. The device of claim 1, wherein:
the housing is a water permeable, elongated, annular tube having an inner diameter from about 2 mm to about 5 mm,
the first unit comprises a first plurality of tablets, each tablet having a diameter substantially the same as the inner diameter of the elongated annular tube, the first plurality of tablets filling a length from about 1 cm to about 3 cm of the lumen of the annular tube, and
the second unit comprises a second plurality of tablets, each tablet having a diameter substantially the same as the inner diameter of the elongated annular tube, the second plurality of tablets filling a length from about 10 cm to about 15 cm of the lumen of the annular tube.

15. The device of claim 14, wherein a ratio of volume of the first plurality to volume of the second plurality is from 0.05 to 0.5.

16. The device of claim 1, wherein the device is configured to spontaneously assume a shape in the absence of a compressive load, which shape comprises an interconnected and overlapping pair of coils.

17. The device of claim 1, wherein a flow modulator channel is disposed in the reservoir between the first unit and the second unit.

18. The device of claim 1, wherein:
the housing is water permeable,
the first unit is a first tablet which comprises gemcitabine,
the second unit is a second tablet that comprises the osmotic agent, and
the housing is configured to release the gemcitabine from the housing by osmotic pressure.

19. The device of claim 18, wherein the osmotic agent comprises urea.

20. A method of administering a drug to a patient, comprising:
inserting the device of claim 1 into a patient; and
releasing the drug from the inserted device.

21. The method of claim 20, wherein the device is inserted into the patient's bladder.

22. The method of claim 21, wherein, following insertion of the device into the patient, urine enters the reservoir and solubilizes the drug and the osmotic agent.

23. The method of claim 22, wherein the drug is gemcitabine and the osmotic agent is urea, and the gemcitabine is released from the device at a zero order rate over a period from 2 to 14 days.

24. An intravesical drug delivery device comprising:
a housing defining a reservoir;
a first unit contained within the reservoir in a first position, the first unit comprising a drug; and
a second unit contained within the reservoir in a second position distinct from the first position, the first position and the second position being in fluid communication with one another,
wherein the second unit comprises an osmotic agent that facilitates in vivo release of the drug from housing,
wherein the device is elastically deformable between a relatively straightened shape suited for insertion through the urethra of a patient and into the patient's bladder and a retention shape suited to retain the device within the bladder, and
wherein the device comprises a plurality of solid first units and a plurality of solid second units.

25. An intravesical drug delivery device comprising:
a housing, wherein the housing is a water permeable elastomeric tube, which comprises (i) a lumen defining a reservoir, and (ii) a drug release orifice in communication with the reservoir;
a plurality of first tablets which comprise a drug, the first tablets being contained within the reservoir at one or more first positions; and
a plurality of second tablets which comprise an osmotic agent that facilitates in vivo release of the drug from housing, the second tablets being contained within the reservoir at one or more second positions which are different from and in fluid communication with the one or more first positions,
wherein the device is elastically deformable between a relatively straightened shape suited for insertion through the urethra of a patient and into the patient's bladder and a retention shape suited to retain the device within the bladder, and
wherein the device is configured, following intravesical insertion, to permit the first tablets and the second tablets to be solubilized by urine diffusing into the reservoir and to release solubilized drug through the drug release orifice by osmotic pressure generated in the reservoir.

26. The device of claim 25, wherein the first tablets are located closer than the second tablets to the drug release orifice.

27. The device of claim 25, wherein the drug comprises gemcitabine and the osmotic agent comprises urea.

28. The device of claim 25, wherein:
the second tablets are positioned within opposed end regions of the reservoir,
the first tablets are positioned within a middle region in the reservoir between the second tablets, and
the drug release orifice is located in a sidewall of the elastomeric tube adjacent to the first tablets.

29. An intravesical drug delivery device comprising:
a housing, wherein the housing is a water permeable silicone tube, which comprises (i) a lumen defining a cylindrical reservoir, and (ii) a drug release orifice in a sidewall of the silicone tube, the drug release orifice being in communication with the cylindrical reservoir;
a plurality of drug tablets which comprise at least 75 percent by weight gemcitabine; and
a plurality of osmotic agent tablets which comprise at least 85 percent by weight urea,
wherein the osmotic agent tablets are positioned within opposed end regions of the cylindrical reservoir and the drug tablets are positioned within a middle region in the cylindrical reservoir between osmotic agent tablets.

30. The intravesical drug delivery device of claim 29, wherein the drug tablets are centered about the drug release orifice.

31. The intravesical drug delivery device of claim 29, wherein the device is configured, following intravesical insertion, to permit the drug tablets and the osmotic agent tablets to be solubilized by urine diffusing into the reservoir and to release gemcitabine through the drug release orifice by osmotic pressure generated in the reservoir.

* * * * *